(12) United States Patent
Sieffert et al.

(10) Patent No.: US 6,275,869 B1
(45) Date of Patent: *Aug. 14, 2001

(54) SYSTEM FOR NETWORK COMMUNICATION OF IMAGE INFORMATION BETWEEN IMAGING DEVICES ACCORDING TO MULTIPLE PROTOCOLS

(75) Inventors: Kent J. Sieffert, Minneapolis; Andrew R. Ihlenfeldt, Saint Paul, both of MN (US)

(73) Assignee: Eastman Kodak Company, Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/720,882

(22) Filed: Oct. 4, 1996

Related U.S. Application Data

(63) Continuation-in-part of application No. 08/343,184, filed on Nov. 22, 1994, now Pat. No. 5,630,101.

(51) Int. Cl.[7] .................................................. G06F 15/00
(52) U.S. Cl. ............................ 709/321; 710/11; 709/229
(58) Field of Search ..................................... 709/229, 246, 709/321; 710/105, 106, 62, 64, 65, 73, 11

(56) References Cited

U.S. PATENT DOCUMENTS 4,604,686    8/1986    Reiter et al. .................... 395/500.46
5,060,140  * 10/1991   Brown et al. ........................ 710/105
5,200,993    4/1993    Wheeler et al. ................... 379/93.02

(List continued on next page.)

OTHER PUBLICATIONS

"Design of the Interface Between the Intensive Care Unit and Hospital/Radiology Information Systems at University of Arizona," Alsafadi et al., *Proceedings of the Annual International Phoenix Conference on Computers and Communications*, Phoenix, AZ, Apr. 12–15, 1994, pp. 404–412.

*Primary Examiner*—Dung C. Dinh
(74) *Attorney, Agent, or Firm*—William F. Noval

(57) ABSTRACT

A medical imaging system for communicating image information between a plurality of different medical imaging modalities having different input protocols and a plurality of different laser imagers having different output protocols takes advantage of a reusable, object-oriented software architecture having a plurality of functionally independent components. The individual components can be configured in a communication pipeline to communicate image information between a medical imaging modality and a laser imager according to desired protocols in a networked manner. Each component can be interchanged with a differently configured component to facilitate communication of image information according to a different protocol, thereby reconfiguring the pipeline to achieve significant flexibility. The software architecture is scalable to produce a plurality of communication pipelines, each of which can be configured according to desired protocols. Thus, the system can support a different protocol by either swapping components to reconfigure a single communication pipeline, or by simply selecting an alternative among a plurality of differently configured communication pipelines in the scalable architecture. The software architecture is equipped with a network executive component designed to configure one or more communication pipelines for network communication.

15 Claims, 5 Drawing Sheets

U.S. PATENT DOCUMENTS

| | | | |
|---|---|---|---|
| 5,303,342 | 4/1994 | Edge | 345/526 |
| 5,329,431 | 7/1994 | Taylor et al. | 362/85 |
| 5,339,413 | 8/1994 | Koval et al. | 709/300 |
| 5,392,393 | 2/1995 | Deering | 345/505 |
| 5,410,675 | 4/1995 | Shreve et al. | 710/65 |
| 5,432,906 | 7/1995 | Newman et al. | 345/501 |
| 5,457,784 | 10/1995 | Wells et al. | 710/9 |
| 5,493,635 | 2/1996 | Brindle et al. | 395/114 |
| 5,502,726 | 3/1996 | Fischer | 370/392 |
| 5,630,101 * | 5/1997 | Sieffert | 709/246 |
| 5,647,056 * | 7/1997 | Barrett et al. | 709/229 |

* cited by examiner

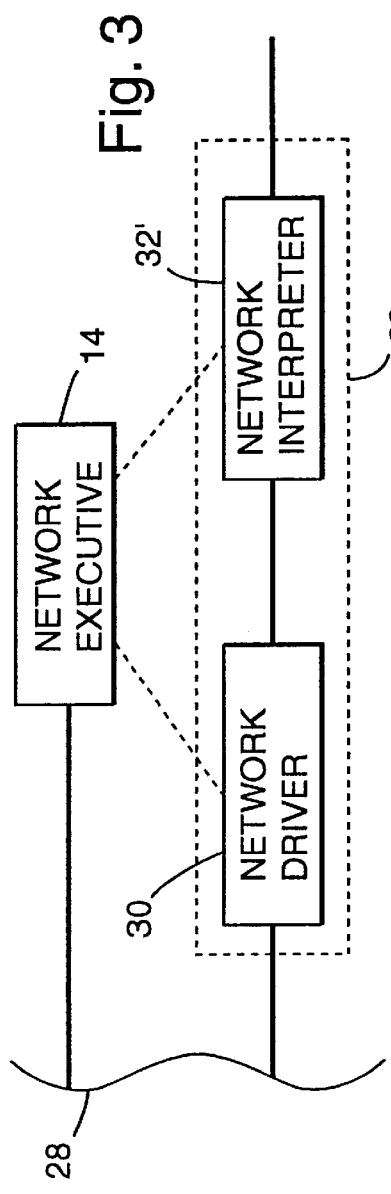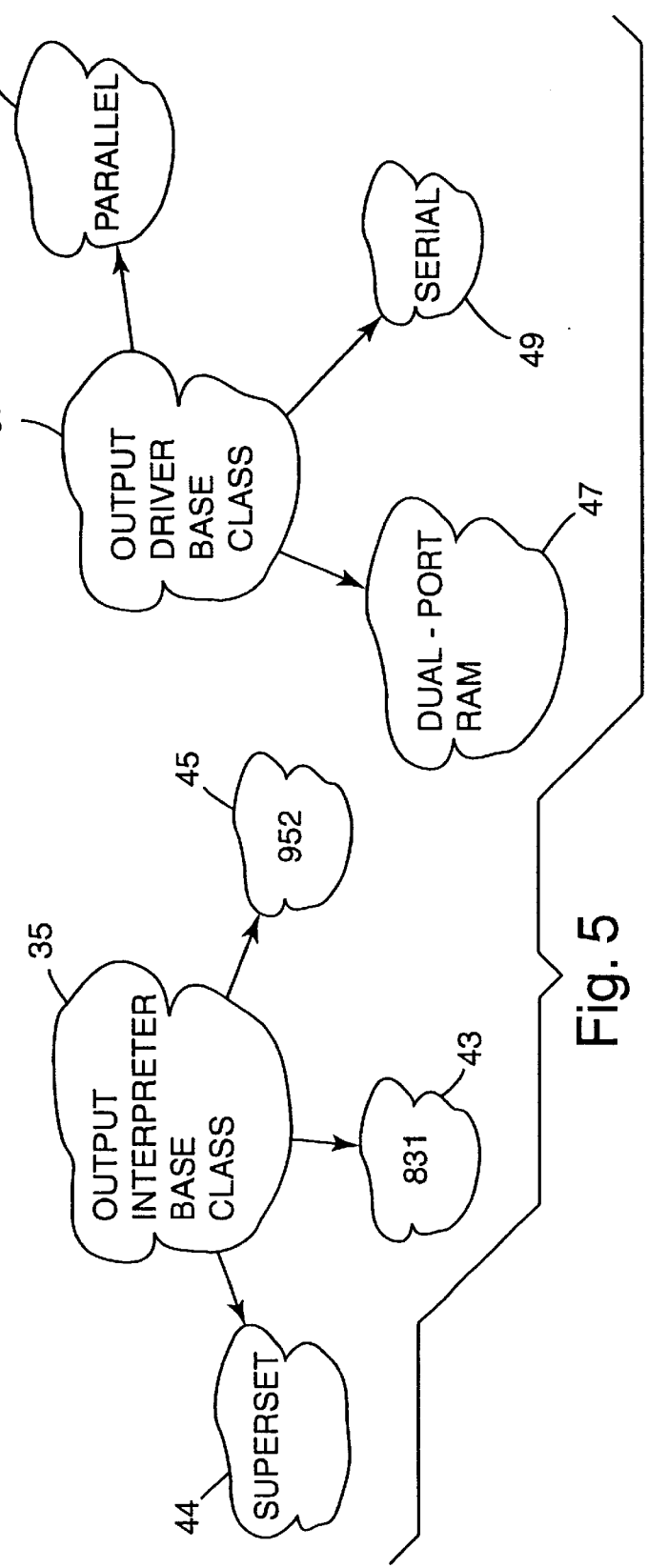

SYSTEM FOR NETWORK COMMUNICATION OF IMAGE INFORMATION BETWEEN IMAGING DEVICES ACCORDING TO MULTIPLE PROTOCOLS

RELATED APPLICATIONS

This application is a continuation-in-part of U.S. patent application Ser. No. 08/343,184 filed Nov. 22, 1994 now U.S. Pat. No. 5,630,101, issued May 13, 1997.

FIELD OF THE INVENTION

The present invention relates to imaging systems, and, more particularly, to systems for communicating image information between an input imaging device and an output imaging device in a network environment.

BACKGROUND OF THE INVENTION

An imaging system typically includes an input imaging device that generates image information, and an output imaging device that forms a visible representation of an image based on the image information. In a medical imaging system, for example, the input imaging device may include a diagnostic device, such as a magnetic resonance (MR), computed tomography (CT), conventional radiography (X-ray), or ultrasound device. Alternatively, the input imaging device may include a user interface device, such as a keypad, mouse, or trackball, which is also capable of generating medical image information. As a further alternative, the input imaging device may include an image archival workstation for retrieving archived image information. The output imaging device in a medical imaging system typically includes a digital laser imager. The laser imager exposes an imaging media in response to the image information to form the visible representation.

The image information generated by the input imaging device includes image data containing digital image values representative of the image, and imaging requests specifying operations to be performed by the laser imager. Each of the digital image values corresponds to one of a plurality of pixels in the original image, and represents an optical density associated with the respective pixel. In response to an imaging request, the laser imager converts the digital image values to generate laser drive values used to modulate the intensity of a scanning laser. The laser drive values are calculated to produce exposure levels, on the imaging media, necessary to reproduce the optical densities associated with the pixels in the original image when the media is developed, either by wet chemical processing or dry thermal processing. The laser imager may perform a number of additional operations in response to the imaging requests generated by the input imaging device. For example, the laser imager may manipulate the image data, prior to generating the laser drive values, to produce a variety of different format and/or appearance characteristics.

The image information processed by the laser imager has a format determined by an input protocol associated with the particular input imaging device. Medical imaging systems typically are capable of handling image information generated according to a variety of diverse input protocols. An input protocol can be characterized as including a network driver protocol, which provides lower-level communications specifications as to a particular input imaging device, and a network interpreter protocol, which determines the format for interpreting image information generated by the input imaging device. The number of different input protocols results, to some degree, from the various types of input imaging devices presently in use, e.g., a magnetic resonance (MR), computed tomography (CT), conventional radiography (X-ray), or ultrasound device, each of which may generate image information according to a different protocol. The primary source of different input protocols is, however, the existence of a number of modalities, i.e., input imaging devices made by different manufacturers and having unique, manufacturer-specific input protocols. For example, manufacturers such as Siemens, Toshiba, GE, and Picker presently make CT-type input imaging devices that provide similar functionality, but which generate image information according to different modality-specific input protocols.

In addition to the ability to handle multiple input protocols, medical imaging systems typically are capable of handling communication of image information to output imaging devices according to multiple output protocols. Like an input protocol, an output protocol can be characterized as including an output driver protocol, which determines requirements for communication with a particular output imaging device, and an output interpreter protocol, which determines the format for translating image information into a form understood by the output imaging device. Different output protocols primarily result from the availability of laser imaging output devices having different sets of functional capabilities. The different sets of functional capabilities present varying complexity that can lead to different output protocols. For example, Imation Enterprise Corp. ("Imation"), of Oakdale, Minn., presently offers laser imagers having different sets of functional capabilities referred to as the "831," "952," and "SuperSet" sets, each of which is associated with a set-specific output protocol.

Existing medical imaging systems presently accommodate multiple input and output protocols on an ad-hoc basis by the design of point-to-point hardware and/or software interfaces specifically configured for a particular input protocol and a particular output protocol. The use of a custom-made interface is extremely inflexible. If communication with a different input imaging device is later required, the entire interface must be redesigned to handle the relationship between the new input protocol and the old output protocol. A change in the output imaging device similarly requires redesign of the interface to handle the relationship between the new output protocol and the old input protocol. Unfortunately, redesign of the interface is a cumbersome task that often requires a significant investment in hardware and/or software development time. Even seemingly minor modifications in functionality of an input or output imaging device can produce numerous, costly design changes that propagate throughout the interface.

One solution to these problems is described in parent U.S. Pat. No. 5,630,101, entitled "System for Communication of Image Information Between Multiple-Protocol Imaging Device." The system described in this patent application adopts an object-oriented, modular design in effecting a software-based direct-connect architecture to allow for significant flexibility in laser imager communication. An interface executive instantiates the needed input driver-input interpreter pair and the needed output interpreter-output driver pair to create a pipeline so that a particular host modality can communicate with a particular laser imager. Each of the input driver, input interpreter, output interpreter and output driver components is a discrete software object, or "black box." In this manner, each can be modified or replaced by a new object without affecting the performance of the others, or the overall pipeline. For example, the input interpreter and driver pair may be specific to a Siemens host modality, while the output interpreter and output driver pair may be specific to an Imation laser imager using the 831 protocol. If the latter pair is replaced with a pair specific to an Imation laser imager using the SuperSet protocol, the design of the components is such that the input interpreter and driver pair does not also need to be replaced.

Although the 5,630,101 patent promotes flexibility in laser imager architecture, it discloses only a direct-connect, point-to-point architecture. For every input-output pair, the interface executive must instantiate a separate input driver-input interpreter pair and output interpreter-output driver pair. That is, the interface executive must create a separate pipeline between each host modality and each laser imager. Although not a misgiving in a system having a relatively small number of host modalities, this can pose a problem in environments where a significant number of host modalities communicate with a plurality of different laser imagers. This is especially true in a networking environment, in which typically a number of network clients all speak the same protocol. In such a situation, it is desirable not to have redundant a input driver-input interpreter pair for each and every client. Besides the drainage in resources, this architecture also places excessive overhead on the interface executive.

Thus, there is an increasing demand for even more flexible medical imaging systems capable of providing communication between a variety of input and output imaging devices having multiple protocols. It is desirable that such medical imaging systems not only provide flexibility with respect to current protocols, but also be capable of adaptation to handle future protocols in a cost-effective manner. There also are increasing demands for network communication of image information between input and output imaging devices. In the medical imaging field, for example, the American College of Radiology (ACR) and the National Electrical Manufacturers Association (NEMA) have formed a joint committee to develop a standard for digital imaging and communications in medicine, known as the DICOM protocol. The DICOM protocol was designed to facilitate connectivity among equipment in the medical industry, particularly in view of the movement of hospitals from point-to-point environments to network environments. Medical equipment manufacturers throughout the industry are now beginning to implement the DICOM communications protocol. The DICOM protocol sets one standard for network communication of image information. However, other network protocols exist and will continue to be created. Thus, protocol translation continues to be necessary in network systems. The need for protocol translation in network systems creates problems similar to those encountered with point-to-point systems. Specifically, flexibility and ease of adaptation for multiple protocols continue to be of concern. Accordingly, there is a need for a system capable of providing network communication of image information between imaging devices according to multiple communication protocols.

SUMMARY OF THE INVENTION

The present invention is directed to a medical imaging system for communicating image information via a network between a plurality of different input imaging devices and output imaging devices according to different communication protocols.

In one embodiment of the invention, a software system for communicating medical image information between at least one of a plurality of different input imaging devices and at least one of a plurality of different laser imagers via a network interface comprises one or more network driver components, one or more network interpreter components, one or more output interpreter components, one or more output driver components, one or more network executive components, and an interface executive component.

Each of the network driver components is configured to receive medical image information from one of the input imaging devices via a network interface. The medical image information is received according to one of a plurality of different network driver protocols. Each of the network driver protocols is specifically associated with one of the input imaging devices.

Each of the network interpreter components is configured to generate first imaging requests based on the medical image information received by one of the network driver components. The first imaging requests are generated according to one of a plurality of different network interpreter protocols. Each of the network interpreter protocols is specifically associated with one of the input imaging devices.

Each of the output interpreter components is configured to generate second imaging requests based on the first imaging requests generated by one of the network interpreter components. The second imaging requests are generated according to one of a plurality of different output interpreter protocols. Each of the output interpreter protocols is specifically associated with one of the laser imagers.

Each of the output driver components is configured to communicate the second imaging requests generated by one of the output interpreter components to one of the laser imagers. The second imaging requests are communicated according to one of a plurality of different output driver protocols. Each of the output driver protocols is specifically associated with one of the laser imagers.

Each of the network executive components communicatively interconnects one of the network driver components and one of the network interpreter components. Furthermore, the interface executive component defines one or more network communication pipelines. Each of the pipelines communicatively interconnects one of the input imaging devices, one of the network executive components, one of the output interpreter components, one of the output driver components, and one of the laser imagers.

The present invention provides for a number of advantages in facilitating communication between the input imaging devices and the laser imagers. Because the network executive components can each facilitate communication of a number of input imaging devices, a separate pipeline is not required for each input imaging device, thereby conserving resources. The network executive components also allow the present invention to facilitate communication between input imaging devices and laser imagers on a network level, as opposed to in a direct-connect manner. Furthermore, the network executive components are delegated responsibility by the interface executive component as to overseeing communication from the input imaging devices. This frees the interface executive component from itself having to take on this responsibility.

In one embodiment of the present invention the software system is constructed in both an object-oriented and client-server manner, and employs remote procedure calls for facilitating communication among components. This gives the invention the benefit of reusability of the components as new components for different protocols are created. Further, this gives the invention the advantage of seamless integration of the components, and promotes scalability of the entire software system. In addition, this gives the present invention the advantage of interchangeability of the components.

Still other and further embodiments, aspects and advantages of the present invention will become apparent in the following description and by reference to the accompanying drawings.

BRIEF DESCRIPTION OF THE DRAWINGS

The accompanying drawings are included to provide a further understanding of the present invention and are incorporated into and constitute a part of this specification. The drawings illustrate embodiments of the present invention and together with the description serve to explain the principles of the invention.

FIG. 3 is a functional block diagram illustrating a subsystem of the medical imaging system of FIG. 1;

FIG. 5 is a diagram illustrating the object-oriented protocol hierarchy that facilitates interchangeability of the output interpreter component and the output driver component; and, FIG. 6 is a functional block diagram of a client-server relationship applicable to the medical imaging system shown in FIG. 1, in accordance with the present invention.

DETAILED DESCRIPTION OF THE DRAWINGS

Overview of the Present Invention

Figure 1:
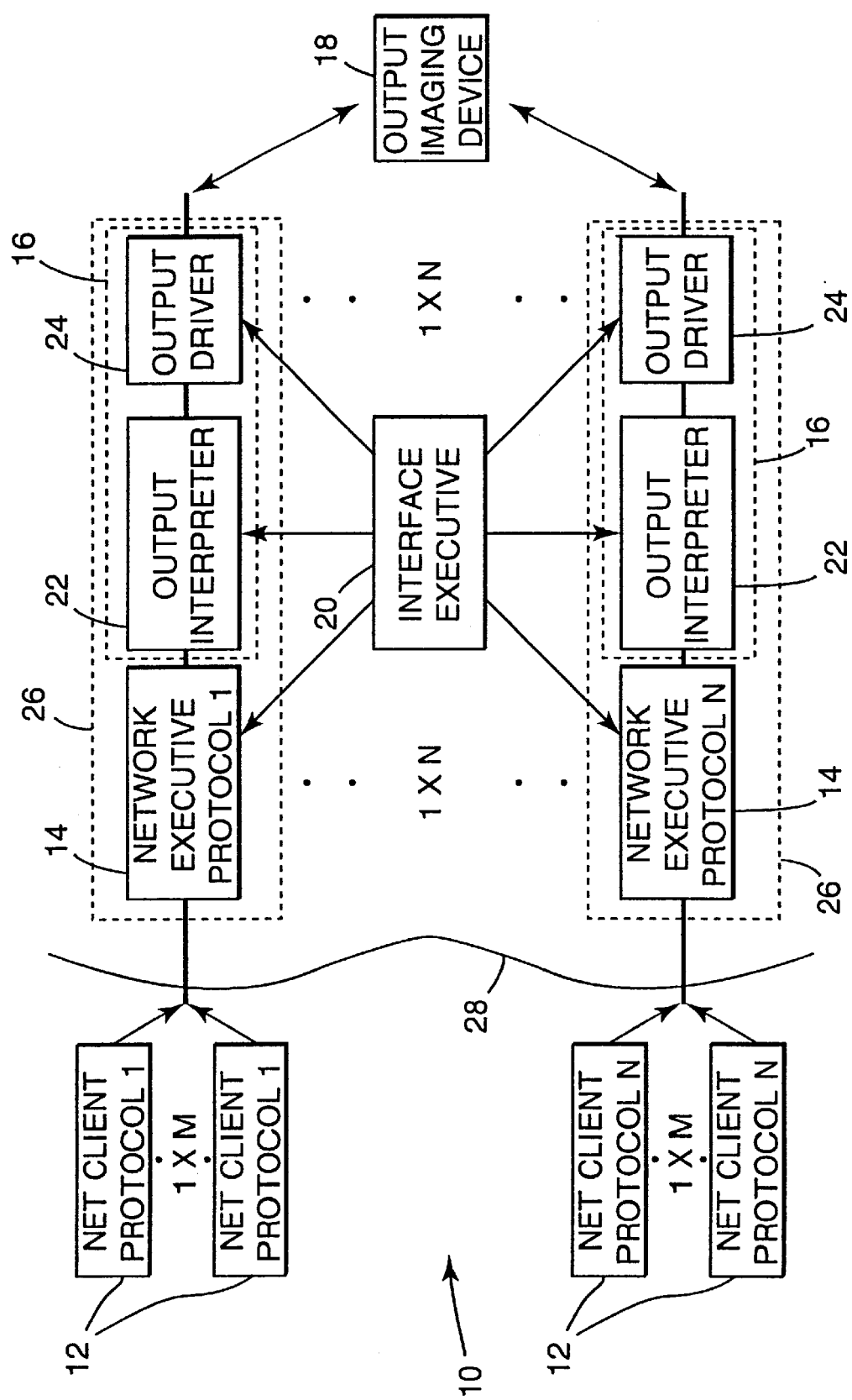
FIG. 1 is a functional block diagram of a medical imaging system for communication of image information between multiple-protocol imaging devices in a network communication environment, in accordance with the present invention.

The present invention effects a scalable software architecture for simultaneously translating multiple medical imaging protocols within a network paradigm. Referring to FIG. 1, a functional block diagram of a medical imaging system 10 for communication of image information between multiple-protocol imaging devices in a network communication environment, in accordance with the present invention, is shown. The system 10 includes a plurality of input imaging devices in the form of network clients 12, one or more network executive components 14, one or more output interface components 16, an output imaging device 18, and an interface executive component 20. Each output interface component 16 includes an output interpreter component 22 and an output driver component 24.

As shown in FIG. 1, each of clients 12 communicates with output imaging device 18 via a particular pipeline 26 specific to a particular protocol. Thus, so long as each of clients 12 speaks the same one protocol, only one pipeline 26 is needed to provide for communication between the clients 12 and output imaging device 18. Further, if each of clients 12 speaks one or two of two different protocols, then two different pipelines are needed; and so on. In this manner, the present invention allows for N different pipelines for N different protocols, in which each pipeline is capable of handling M different clients speaking that particular protocol. That is, a separate pipeline for each client is not required, but rather only for each different protocol.

Each pipeline 26 comprises three primary components: a network executive component 14, an output interpreter component 22 and an output driver component 24, the latter two of which are paired as a single output interface component 16. Broadly speaking, the system shown in FIG. 1 is set up in the following manner. For every output imaging device 18, the interface executive component 14 creates a separate pipeline 26 for each separate protocol spoken by at least one network client 12 that may communicate with imaging device 18. The interface executive component 14 accomplishes this by instantiating a network executive component 14 specific to the protocol spoken by one or more clients 12, and an output interface component 16 specific to output imaging device 18, a pair of particular components 14 and 16 thus making up a particular pipeline 26. This creation of pipelines 26 can occur either "on the fly" as clients speaking different protocols enter or leave the network of system 10, or can occur when the network is first being initialized. The present invention is not limited either way.

Upon establishment of the pipelines 26, a client 12 speaks to the output imaging device 18 in general terms in the following manner. Network executive component 14 filters and interprets requests received from client 12 to corresponding first requests that output interface component 16 understands. Upon transmission to interface component 16, the first requests are further filtered and interpreted, to the particular corresponding second requests that output imaging device 18 understands. In this manner, the present invention takes requests specific to a particular protocol, translates them into first requests, and further translates them into second requests specific to a particular imaging device. Thus, component 14 and component 16 can be changed independent of one another, because both speak to one another via first requests. Put another way, the implementation of a network executive component 14 specific to a particular protocol is independent of any imaging device 18, while the implementation of output interface component 16 is independent of any given protocol spoken by a particular client 12. Note as well that this process as described is operable in reverse, such that requests from device 18 can be sent to client 12.

The present invention thus adopts a pipeline model for allowing communication between M clients speaking N protocols to an imaging device. The interface executive component manages creation of these pipelines. A pipeline is created for each particular protocol spoken by at least one of M clients on the network. Because typically N<<M, the present invention conserves resources over a system in which a separate pipeline is necessary for each client, not each protocol. This is a significant advantage of the present invention.

Figure 2:
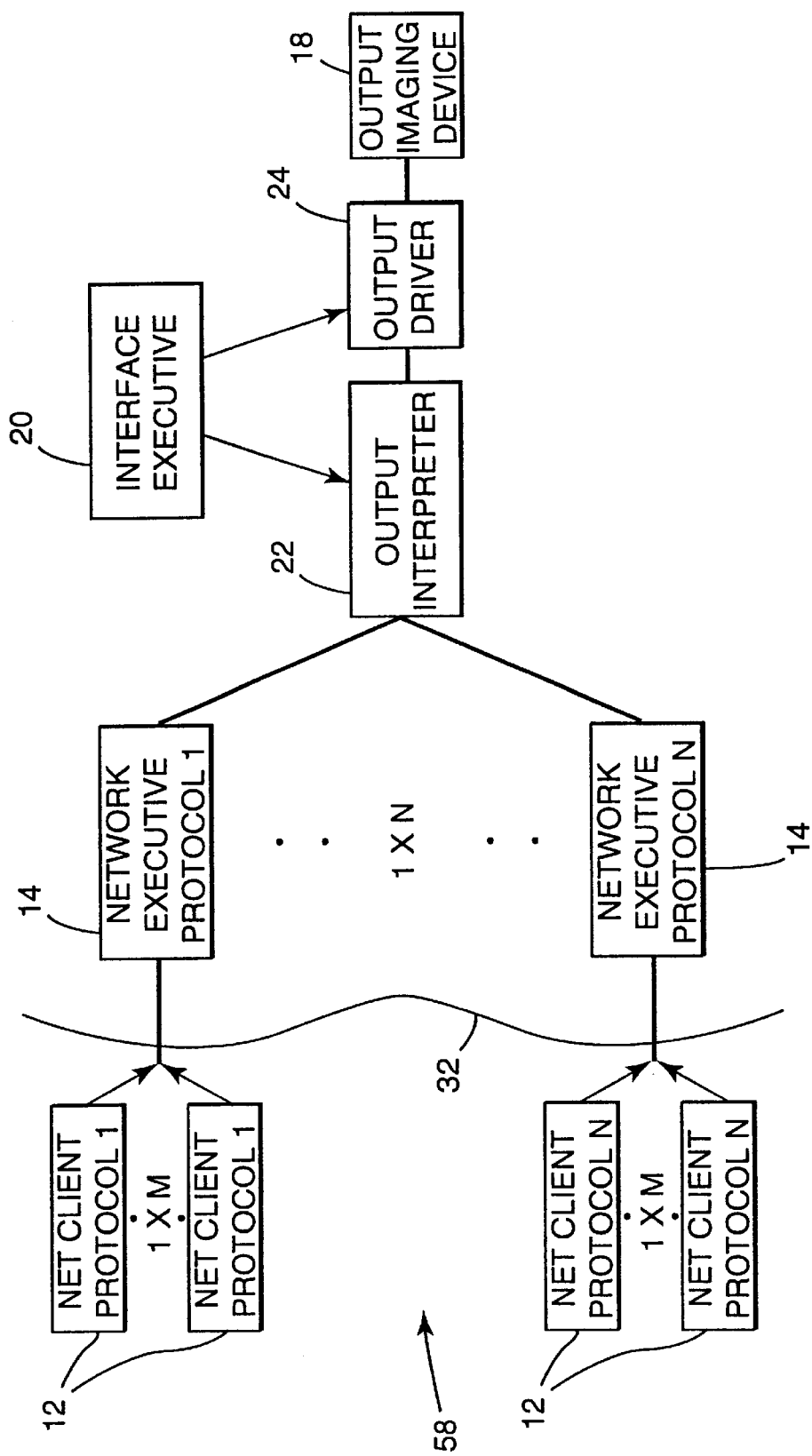
FIG. 2 is a functional block diagram of an alternative medical imaging system for communication of image information between multiple-protocol imaging devices in a network communication environment, in accordance with a further embodiment of the present invention.

Referring now to FIG. 2, a functional block diagram of a further embodiment of the present invention is shown. Like-numbered elements of FIG. 2 as compared to FIG. 1 indicate that the elements are identical, and that description of them in conjunction with FIG. 1 applies equally in conjunction with FIG. 2. As an alternative to instantiating N full translation pipelines, the interface executive component may be configured to instantiate one translation pipeline with N network executive components operating independently and in parallel to one another. In this manner, N×M clients may be supported without the inefficiency of providing N-1 output interpreter components and N-1 output driver components. The system 58 of FIG. 2 supports N network protocols and N×M network clients with the implementation of only one communication pipeline. System 58 includes a plurality of network executive components 14 that listen for network clients 12 having particular network protocols. The interface executive component 20 communicatively interconnects each of network executive components 14 with a single output interpreter component 22, a single output driver component 24, and a single output imaging device 18 to provide a single communication pipeline with multiple, protocol-specific network inputs.

Thus, the embodiment of the present invention as shown in FIG. 2 varies from that shown in FIG. 1 in that the former embodiment conserves even more resources than does the latter. In the case where there is one output imaging device but multiple network protocols, the embodiment shown in FIG. 1 wastes some resources by providing redundant output interface components 16 for each pipeline 26, which are all redundant due to the fact that there is only one output imaging device. This redundancy, and corresponding waste of resources, is eliminated by the embodiment shown in FIG. 2. In FIG. 2, there is only one pipeline 26, and only one output interface component 16, to which each of network executive components 14 is coupled. Other than this redundancy reduction, FIG. 2 operates identically to FIG. 1, and description made in conjunction with FIG. 1 should be referred to for description of FIG. 2.

Implementation of the Present Invention

Referring again to FIG. 1, the network executive components 14, output interface components 16, and interface executive component 20 are implemented in one embodiment as an object-oriented software system that interfaces with a network having network clients 12 and output imaging device 18. The software system may be implemented as part of an output imaging device 18, such as a continuous tone digital laser imager, or as part of a discrete interface device controlling communication of image information between network clients 12 and output imaging device 18.

In one embodiment of the invention, the network comprises a plurality of different clients, such as magnetic resonance (MR), computed tomography (CT), conventional radiography (X-ray), and ultrasound devices, manufactured by a number of different manufacturers, such as Siemens, Toshiba, GE, or Picker. The laser imager can be any of a number of different imagers, such as those manufactured by Imation and that understand the 831, 952, or SuperSet protocols. The laser imager may also reside directly on the network, in which case the software system typically resides on a hardware card inserted into the laser imager. The card typically comprises input/output (IO) circuitry, as well as memory such as a ROM or flash ROM, which is one type of reprogrammable ROM. The software system resides on this memory.

In the alternative, the laser imager does not reside directly on the network, and instead is coupled to the network via an intermediary computer that itself resides directly on the network. The intermediary computer typically has a random-access memory (RAM), a read-only memory (ROM), a central-processing unit (CPU) and a storage device, such as a hard disk drive, programmable ROM, or disk drive. In this case, the software system typically resides on the storage device of the intermediary computer, and is copied into RAM and executed therefrom by the CPU. Where the storage device is a disk drive or other removable storage device, the software system can be stored on the storage medium for insertion into the device. The present invention is not, however, limited to any particular hardware implementation.

The image information generated by the input imaging devices associated with network clients 12 includes both requests for imaging operations, and image data containing digital image values representative of an image to be handled by output imaging device 18. For purposes of this description, pipeline 26 will be described as handling communication of image information in the form of imaging requests, with image information in the form of digital image values representative of the image being communicated by a separate communication path. It is within the scope of the invention, however, that pipeline 26 could be configured to handle communication of image information in the form of both requests for imaging operations and image data containing the digital image values.

In a typical medical imaging system, imaging requests include requests to initiate an image print job by output imaging device 18, requests to abort a previously initiated image print job, requests to define or modify a format of an image to be printed, requests to delete a set of image data representative of a previously acquired image, and requests to store image data in a particular image location.

Components of the Invention: Interface Executive Component

The interface executive component 20 defines one or more (1 to N) communication pipelines 26. Each communication pipeline 26 communicatively interconnects, or "binds," one or more of the M network clients 12, one of network executive components 14, one of output interpreter components 22, one of output driver components 24, and output imaging device 18 in a bi-directional manner. The output imaging device 18 may communicate with any of pipelines 26 on a shared basis. Alternatively, a plurality of output imaging devices 18 could be provided, each being communicatively interconnected with a particular pipeline 26.

The interface executive component 20 provides for the highest level of intelligence within system 10 of FIG. 1. It governs and manages the particular network components 26 and output interface components 16 needed for clients 12 to communicate with device 18. That is, as shown in FIG. 1, based on the N different protocols spoken by clients 12, the interface executive component 20 instantiates a particular pipeline 26 made up of a network executive component 26 and output interface component 16. Furthermore, if there are P different output imaging devices (as opposed to just one, as shown in FIG. 1), then the interface executive component instantiates N×P different pipelines, one for every unique imaging device-protocol pair. This can be accomplished in a separate set-up mode, or "on the fly" as clients speaking different protocols enter or leave the network.

Although having the most intelligence of any component within the present invention, the interface executive component 20 differs from the interface executive component disclosed and described in U.S. Pat. No. 5,630,101 in that it has less intelligence than the interface executive component disclosed in that patent application. The interface executive component disclosed and described in U.S. Pat. No. 5,630,101 instantiates an input interface component particular to every client needing to communicate with a particular imaging device. That is, the interface executive component constructs a pipeline on a client-by-client basis. Conversely, the interface executive component of the present invention instantiates a network executive component 14 specific to a particular protocol, and thereto delegates all responsibility of serving network clients. Thus, the interface executive component of the present invention constructs a pipeline on a protocol-by-protocol basis. It therefore has less intelligence in that it does not micromanage communications with particular clients as does the interface executive component of U.S. Pat. No. 5,630,101. That is, the latter interface executive component "knows" all details regarding the input device, whereas the interface executive component of the present invention simply "knows" that there are input devices residing on a network, and delegates responsibility for handling implementation of the interface as to the input devices to the network executive component 14.

The interface executive component 20 defines the structure of pipeline 26. The pipeline 26 is configured to communicatively interconnect a number of components 30, 32 (which are shown in FIG. 3 and, as shown there and as will be explained later, are instantiated by network executive component 14), 22 and 24 having different protocols on a selected basis to provide significant flexibility. This flexibility provides a medical imaging system 10 capable of achieving communication between a variety of different network clients 12 and one or more output imaging devices 18 having a variety of different functional capabilities. Thus, interface executive component 20 treats each functionally independent component 14, 22 and 24 as a "black box" with a clearly identified set of responsibilities and a defined interface. The interface executive component 20 selects the appropriate series of black boxes based on the environment, and binds them together with "handles" to one another to form the complete pipeline 26. As a further advantage, interface executive component 20 in one embodiment is configured to dynamically bind the components "on the fly" to form a communication pipeline 26 appropriate for the current imaging environment. Moreover, interface executive component 20 is configured to produce a scalable software architecture having a plurality of communication pipelines 26 configured according to different protocols. The scalable architecture enables output imaging device 18 to communicate simultaneously with several network clients 12 on a shared basis using the necessary protocols, as provided by each pipeline 26. Alternatively, a plurality of output imaging devices 18 can be provided, each being communicatively interconnected with a particular pipeline 26.

Thus, the interface executive component 20 scales the software architecture to match the requirements of the environment, creating as many network executive components and pipelines as there are different network protocols. The interface executive component 20 selectively binds a series of components 14, 22 and 24 having specific protocols necessary to match a particular network client 12, a particular output imaging device 18, and the required hardware interfaces.

Components of the Invention: The Network Executive Components

The network executive component 14 is responsible for handling all network clients 12 that communicate via a particular protocol. As shown in FIG. 1, a network executive component 14 is provided for each particular one of N network protocols. Thus, network executive component 14 handles multiple network clients 12 simultaneously. The interface executive component 20 delegates to network executive component 14 the responsibility of managing all network-specific services. The interface executive component 20 instantiates a particular network executive component 14 for each medical imaging network protocol that will be supported on the network by system 10. If the Picker Networking Protocol is to be supported, for example, interface executive component 20 instantiates a network executive component 14 capable of serving such a protocol. For further example, the interface executive component 20 also instantiates another network executive component capable of serving the DICOM protocol, if that protocol is to be supported.

The network executive component 14 governs all objects needed to manage network communication. The primary function of network executive component 14 is to monitor or "listen" at network interface 28 for imaging requests from network clients 12 having a particular network protocol. When a network client 12 requests access to output imaging device 18 via a particular network protocol, network executive component 14 spawns a network driver component 30 and a network interpreter component 32 appropriate for that protocol, as shown in FIG. 3. Further, network executive component 14 binds network driver component 30 to network interpreter component 32, and then binds network interpreter component 32 to output interpreter component 22 using handle information previously provided by the interface executive component 20. The network executive component 14 then returns to listening to network interface 28 for new requests sent according to the particular network protocol. The network driver component 30 and network interpreter component 32 together form a network interface component 33, as is also shown in FIG. 3.

The presence of the network executive component in the present invention serves as a distinguishing characteristic of the invention over U.S. patent application Ser. No. 08/343,184. In application Ser. No. 08/343,184, there is no corresponding network executive components, but rather there are input interface components. The input interface component, however, is not an intelligent component as is the network executive component of the present invention. Rather, an input interface component is instantiated by the interface executive for every connection between a particular client and the imaging device. Conversely, in the present invention the interface executive delegates responsibility for client communication to a network executive component, which itself instantiates other components as necessary for one or more clients speaking a common protocol to communicate with the imaging device.

The network executive components thus provide the present invention with the advantage of network communication in a resource use-minimizing manner. For example, overlaying the system disclosed in U.S. Pat. No. 5,630,101 onto a network of clients results in the creation of pipelines for each of the clients. However, by incorporating client communication in an intelligent network executive component 14, the present invention eliminates the need for the creation of pipelines for each of the clients, but rather only calls for the creation of a pipeline for each of the protocols via which the clients can communicate. Because the number of communication protocols is typically far less than the number of clients, this results in a significant savings in resource use. Furthermore, by delegating the responsibility for client communication to the network executive component 14, the interface executive component 20 is freed from such micromanagement duties, which may otherwise overburden the interface executive component.

In one embodiment, network driver and network interpreter components 30 and 32 as shown in FIG. 3 are instantiated "on the fly" in response to detection by network executive component 14 of a network client 12 having a specific protocol at network interface 84, thereby conserving the hardware/software resources necessary to support such components until needed. This dynamic instantiation of the network driver and network interpreter components 30, 32 enables reduction in the amount of system overhead that otherwise would be necessary. If resource conservation is not a concern, such components are alternatively provided on a permanent basis to provide a fixed, dedicated pipeline 26 for each protocol.

Once the network driver component 30 and network interpreter component 32 have been created, network executive component 14 delegates all responsibility for serving the particular network client 12 to the driver/interpreter pair. The network executive component 14 communicatively binds network client 12, network driver component 30, and network interpreter component 32 to one of output interpreter components 22, using handle information previously provided to the network executive component 14 by the interface executive component 20.

Each of network driver components 30 is configured to receive the image information from a network client 12 according to one of a plurality of different network interface protocols. Each network interface protocol is specifically associated with one of network clients 12, and reflects the modality-specific requirements for communication with the particular network client. Each of the network interpreter components 30 is configured to generate first imaging requests according to one of the network interface protocols based on the content of the received image information. The first imaging requests are generated by network interpreter component 32, and correspond to imaging requests generated by network client 12. The first imaging requests are communicated to output interface component 16.

Each of the network interface protocols includes both a network driver protocol applicable to network driver components 30 and a network interpreter protocol applicable to network interpreter components 32. The appropriate network driver protocol is determined by the communication requirements of a particular network client 12, whereas the appropriate network interpreter protocol is determined by the image information format of the particular input imaging device associated with the network client. The image information format refers to the types of imaging requests generated according to the protocol of a particular input imaging device. The network driver protocol specifies the manner in which a network driver component 30 should carry out the transfer of image information from an input imaging device associated with a network client 12. The network interpreter protocol specifies the manner in which network interpreter component 32 should interpret the image information to generate the first imaging requests. The network driver and network interpreter protocols can vary significantly according to differences in the type of network client 12, as well as the manufacturer of the input imaging device 18.

The network interpreter component 32 also shares a common set of tasks with other network interpreter components, without regard to a specific network interpreter protocol. Primarily, after obtaining image information from a network driver component 30, a network interpreter component 32 analyzes requests contained in the image information and translates them to generate first imaging requests corresponding to operations provided by output imaging device 18. The first imaging requests include requests for a variety of common imaging services provided by output imaging device 18.

The manner in which network interpreter component 32 interprets the requests generated by network client 12 may vary according to the specific network interpreter protocol. The network interpreter component 32 understands the precise format, instructions, and timing constraints inherent in the image information generated by a particular network client 12. Nevertheless, all network interpreter components 22 still provide a common, basic function of generating first imaging requests. The network interpreter component 32 sends the first imaging requests along pipeline 26. Once the first imaging requests have been processed by downstream components in bi-directional pipeline 26, and a response has been received, network interpreter component 32 forms an appropriate response for network client 12. The network interpreter component 32 sends the response along pipeline 26 to network client 12, via network driver component 30, which handles communication requirements necessary to transmit the response to the input imaging device.

The network driver component 30 and network interpreter component 32 have been described in recognition that a network interface component 33 could alternatively be implemented as a single, integral software module. In the embodiment described, however, a network interface component 33 is realized by a discrete network driver component 30 and a discrete network interpreter component 32. A discrete implementation of the sub-components divides the functionality of each network interface component 33 into smaller packages for better modularity. Thus, as an example, with added modularity, changes in hardware specifications for network interface 28 require only reconfiguration of network driver component 30, instead of the entire network interface component 33.

Furthermore, notwithstanding functions specific to a particular protocol, components 30 and 32 of like type (i.e., all network driver components) are configured to perform several common tasks. For example, network driver components 30 share a set of common tasks necessary to communicate with a network client 12 operating according to particular network protocol. A network driver component 30 is configured to handle any hardware specifics such as interrupts, buffers and handshaking necessary to transfer imaging information to and from a particular network client 12. The network driver component 30 is further configured to handle any other specific needs of a network client 12, such as packetizing or initialization. The network driver component 30 performs all necessary communications tasks, isolating the remainder of pipeline 26 from any knowledge of the specific requirements for communication with the network client 12. Thus, the responsibility of network driver component 30 is two-fold. First, network driver component 30 receives image information off the network from network client 12, and prepares the image information for the next stage of pipeline 26, i.e., network interpreter component 32. Second, network driver component 30 transmits any responses emerging from bi-directional pipeline 26 onto the network for communication to network client 12.

Components of the Invention: Output Interface Components

Still referring to FIG. 1, each of output interface components 16 is configured to generate second imaging requests according to one of a plurality of different output protocols, via one of output interpreter components 22, based on the content of the first imaging request. The second imaging requests represent the content of the first imaging requests, as translated by output interpreter component 22 for communication to output imaging device 18. Each output interface protocol is specifically associated with the type of output imaging device 18 and, like the network interface protocol, reflects the requirements for communication with the particular output imaging device. In addition, each of the output interface components 16 is configured to communicate the second imaging requests to output imaging device 18, via output driver component 24, according to one of the output interface protocols.

Each of the output interface protocols includes an output interpreter protocol applicable to output interpreter components 22 and an output driver protocol applicable to output driver components 24. The output driver protocol is determined by the communication requirements of output imaging device 18, whereas the appropriate output interpreter protocol is determined by the image information format of the output imaging device. The output interpreter protocol specifies the manner in which output interpreter component 22 should interpret first imaging requests to generate second imaging requests in a form understood by output imaging device 18. The output driver protocol specifies the manner in which an output driver component 24 should carry out the transfer of second imaging requests to output imaging device 18. Like the network interface protocols, the output interface protocols are subject to variation. For example, both the output driver and output interpreter protocol can vary according to the type of functional capabilities provided by output imaging device 18, e.g., 831, 952, or SuperSet in the case of a laser imager manufactured by Imation.

An output interpreter component 22 is configured to receive, via pipeline 26, first imaging requests generated by a network interpreter component 32, and to interpret the first imaging requests to generate second imaging requests, which conform to the particular protocol required by output imaging device 18. The second imaging requests correspond to the first imaging requests in substance, but are configured according to the output protocol understood by output imaging device 18. Thus, the second imaging requests serve as requests for the same imaging services specified by first imaging requests. The manner in which an output interpreter component 22 interprets the instructions may vary according to the specific output interpreter protocol dictated by output imaging device 18, but all output interpreter components 22 share a common task of generating second imaging requests in a protocol understood by the output imaging device. The output interpreter component 22 sends the second imaging requests along pipeline 26. When output imaging device 18 processes the second imaging requests and formulates a response received via pipeline 26, output interpreter component 22 removes any output protocol-specific information and forms an appropriate response for network interpreter component 32.

Referring now to the output driver component 24, like network driver components 30, all output driver components 24 perform a common set of communication tasks. Specifically, an output driver component 24 is configured to handle any hardware specifics such as interrupts, buffers, and handshaking necessary to transfer imaging information to and from a particular output imaging device 18. The output driver component 24 isolates the remainder of pipeline 26 from any knowledge that communication with output imaging device 18 is carried out via a serial interface, a parallel interface, or a dual-port RAM, etc. The output driver component 24 transmits second imaging requests generated by an output interpreter component 22 to output imaging device 18, maintaining any communication requirements. Further, output driver component 24 receives responses from output imaging device 18, and prepares the response for transmission to output interpreter component 22 via bi-directional pipeline 26.

The output interpreter component 22 and the output driver component 24 have been described in recognition that an output interface component 16 could alternatively be implemented as a single, integral software module. In the embodiment described, however, an output interface component 16 is realized by a discrete output interpreter component 22 and a discrete output driver component 24. A discrete implementation of the sub-components divides the functionality of each interface component 16 into smaller packages for better modularity. Thus, as an example, with added modularity, changes in hardware specifications for interface component 16 require only reconfiguration of output driver component 24, instead of the entire interface component 16.

Object-Oriented Nature of the Components

To facilitate the interchangeability of the components, as has been described, the software interfaces between components 30, 32, 22 and 24 must be pre-defined to make each type of component generic. At the same time, however, an individual component 30, 32, 22 and 24 must be configured to implement functions specific to a particular protocol. Object-oriented techniques, particularly that of inheritance, are used by the present invention to develop a generic base-class protocol for each type of component (e.g., network driver component 30).

Inheritance is a particular object-oriented technique that serves as a mechanism for creating new classes from an existing class. A new class looks similar to an existing class except that it differs from the existing class in a small way; inheritance is employed to define the new class in terms of the existing class. The existing class that serves as a source for inheritance is referred to as a base class, and the new class derived from the base class is referred to as the derived class. An existing class can serve as a base class to more than one derived class. The base class is a definition of a more generic class of software objects, while the classes derived from the base class define more specific or specialized cases of the objects. Thus, the generic base-class protocol specifies the functions provided by a component and the procedures for accessing such functions. Each specific protocol component "inherits" from the corresponding base class protocol, and implements the interface to conform to the environment.

Class inheritance allows the members of one class to be used as if they were members of a second class. No additional programming is required to implement the subclass, except for those operations that either extend or replace the members inherited from the other classes. As that object-oriented system is developed, subclasses are constructed out of existing classes until the appropriate functionality is developed. The construction of subclasses results in the formation of a class hierarchy. The class hierarchy is rooted in the base class, which contains a minimal set of behavior common to all subclasses.

In accordance with the present invention, each component 30, 32, 22 and 24 is configured according to a specific protocol, but also serves as a sub-class of the base class protocol. Because each component 30, 32, 22 and 24 inherits from the base-class protocol and implements a minimal set of functions such that they meet base-class requirements, it can be directly interchanged with any other component of like type that inherits from the same base-class protocol. The interchangeability resulting from the object-oriented techniques produces a "direct-connect" software architecture in which each component can be effectively plugged into pipeline 26 without the need for additional interface development.

Figure 4:
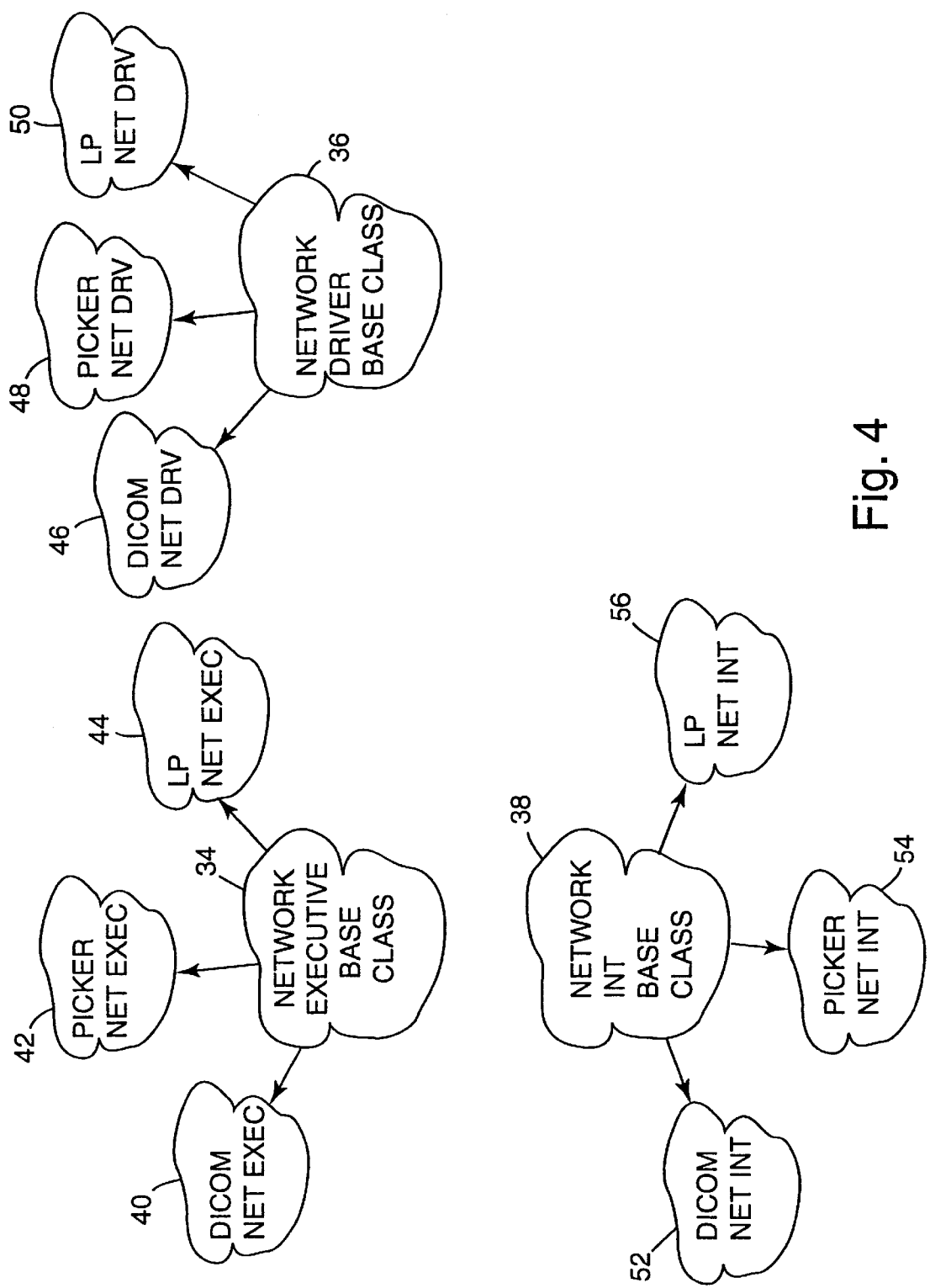
FIG. 4 is a diagram illustrating the object-oriented protocol hierarchy that facilitates interchangeability of the network protocol components, including both the network driver component and the network interpreter component.
Figure 6:
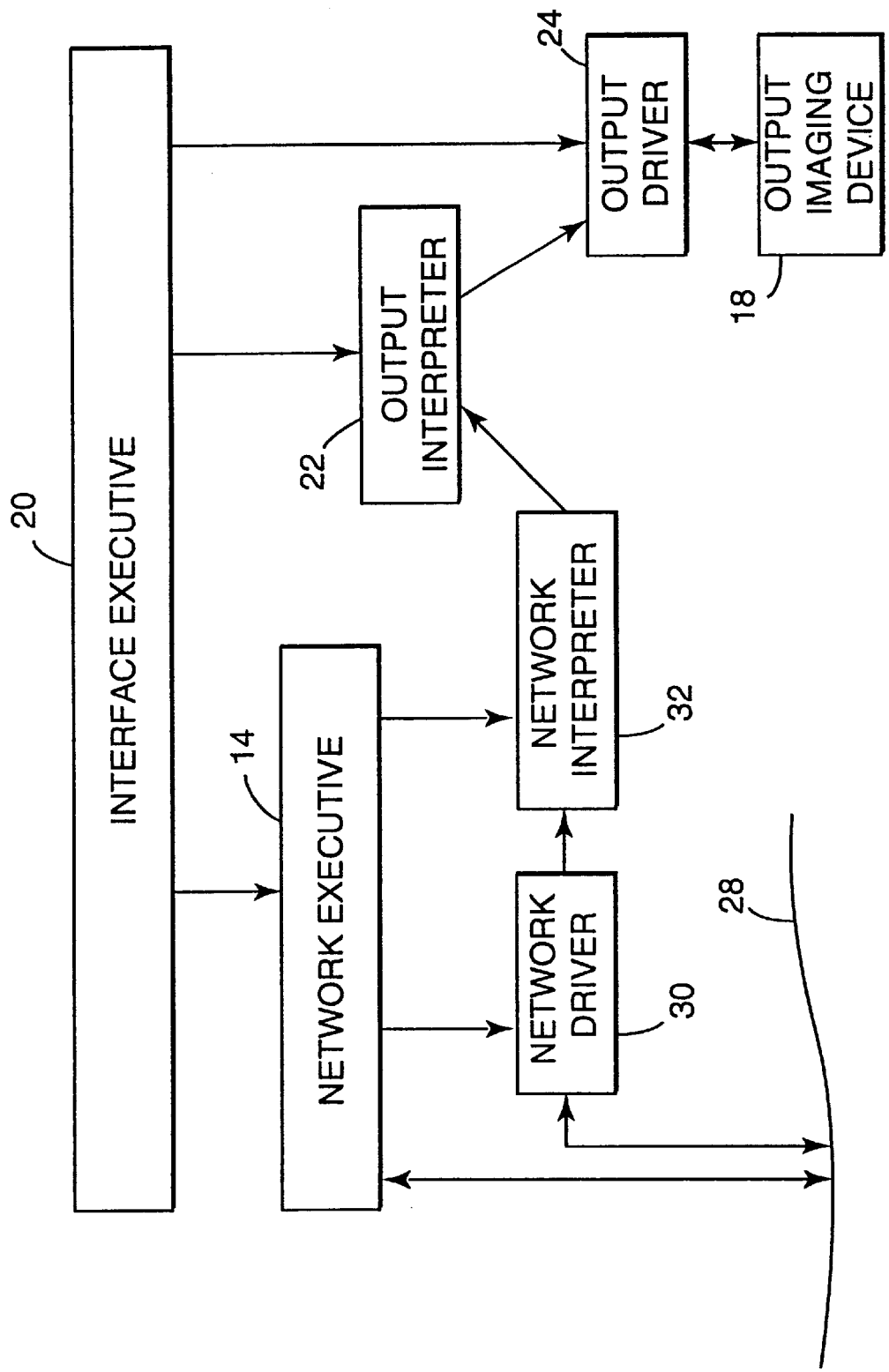

FIGS. 5 and 6 provide an example of an object-oriented protocol hierarchy that facilitates interchangeability of components 30, 32, 22 and 24. The protocol hierarchy illustrates the implementation of components 30, 32, 22 and 24 for specific protocols that as a derived class each "inherit" from a generic base-class protocol. As shown in FIG. 4, a network executive base-class protocol 34 may encompass a plurality of "inheriting" network executive protocols 40, 42, 44 for different network clients 12 such as, for example, DICOM, Picker, and LP that allow an appropriately-instantiated network executive component 14 to detect the presence of a particular network client. Similarly, a network driver base protocol 36 may encompass a plurality of "inheriting" network driver protocols 46, 48, 50 for different network interface requirements associated with a network client 12 such as, for example, DICOM, Picker, or LP. A base-class network interpreter protocol 38 may encompass a plurality of inheriting network interpreter protocols 52, 54, 56 for different types of input imaging devices or manufacturers associated with network clients 12 such as, for example, DICOM, Picker, and LP.

As shown in FIG. 5, a base-class output interpreter protocol 35 may encompass a plurality of inheriting output interpreter protocols for different types of output imaging devices 18, such as an Imation SuperSet output interpreter protocol 41, an Imation 831 output interpreter protocol 43, or an Imation 952 output interpreter protocol 45. Finally, a base-class output driver protocol 37 may encompass a plurality of inheriting output driver protocols for different hardware interface requirements associated with output imaging device 18, such as a dual-port RAM output driver protocol 47, a serial output driver protocol 49, or a parallel output driver protocol 51. Each of the inheriting protocols described above includes protocol-specific functions provided by a component 30, 32, 22 and 24, but implements such functions via a generic interface that inherits from the corresponding base-class protocol 34, 35, 36, 37, 38. For each base-class protocol 34, 35, 36, 37, 38, described above, a variety of additional inheriting protocols can be implemented, according to the requirements of the medical imaging system environment.

Therefore, the nature of components 30, 32, 22 and 24 enables them to be selectively "swapped" in or out of a pipeline 26 in a modular fashion by interface executive component 20. Each of the components 39, 32, 22, 24 is made interchangeable with another component of like type, but different protocol, by a series of software interfaces. This base-class interface is in one embodiment built into each component such that any component 30, 32, 22 and 24 in a pipeline 26 can be replaced without affecting the configuration of the other components in the pipeline. Thus, individual components 30, 32, 22 and 24 also can be reused, significantly reducing costs previously associated with redesign efforts.

For example, if pipeline 26 were to be configured for communication between Siemens network clients 12 and an output imaging device 18 implementing Imation SuperSet functionality, interface executive component 20 would first instantiate a network executive component 14 configured to monitor the presence of Siemens network clients. Upon detection of a Siemens network client 12, network executive component 14 would spawn a network driver component 30 and network interpreter component 32 configured to operate according to the Siemens network protocol. Specifically, network driver component 30 would be configured to operate according to a network driver protocol appropriate for receiving imaging information from the Siemens network client 12. The network interpreter component 32 would operate according to a network interpreter protocol appropriate for generation of first imaging requests based on the format of the image information received from the Siemens network client. The network executive component 14 then would communicatively bind the network driver component 30 and network interpreter component 32 with an output interpreter component 22 having an output interpreter protocol appropriate for generation of second imaging requests understood by the Imation SuperSet output imaging device, the network interpreter component 32 already being bound to an output driver component 24 having an output driver protocol appropriate for communication of the second imaging requests via a serial hardware interface associated with the Imation SuperSet output imaging device.

Alternatively, if a pipeline 26 were to be configured for communication between a Toshiba network client 12 and an Imation SuperSet output imaging device 18, it would only be necessary to "swap" the network driver component 30 and network interpreter component 32 with components configured according to network driver and network interpreter protocols, respectively, appropriate for the Toshiba modality. Specifically, a network executive component 14 instantiated to listen for Toshiba network clients 12 would spawn a network driver component 30 and network interpreter component 32 configured to operate according to the Toshiba protocol. The output interface component 16 used for Siemens network clients 12 could be replicated and used in a separate communication pipeline 26 for Toshiba network clients. The output interface component 16 would include an Imation SuperSet-configured output interpreter component 22 and an Imation SuperSet serial-configured output driver component 24, and therefore would already be configured according to the requirements of output imaging device 18, independently of the protocol of network client 12. Thus, network executive component 14 would communicatively bind in a separate pipeline 26 the network driver and network interpreter components 30 and 32 with the standard output interpreter and output driver components 22 and 24 configured for the Imation SuperSet output imaging device, and useful in any pipeline having a SuperSet output device, and which are already bound to one another.

As another alternative, if the pipeline 26 described above were to be modified for communication between a Toshiba network client 12 and an Imation 952 output imaging device 18, only modification of output interface component 16 would be necessary. Specifically, network executive component 14 would communicatively bind the network driver component 30 and network interpreter component 32 with an output interpreter component 22 having an output interpreter protocol appropriate for generation of second imaging requests understood by the Imation 952 output imaging device, which is already bound to output driver component 24 having an output driver protocol appropriate for communication of the second imaging requests via a serial hardware interface associated with the Imation 952 output imaging device. Thus, the network driver and interpreter components 30, 32 spawned by network executive component 14 would be unaffected by a change in the output imaging device 28 associated with communication pipeline 26.

Finally, if the pipeline 26 described above were to be modified for communication between a Toshiba network client 12 and an Imation 952 output imaging device 18, having a dual-port RAM interface, only modification of output interface component 16 would be necessary. Specifically, network executive component 14 would communicatively bind the network driver component 30 and network interpreter component 32 to an output interpreter component 22 having an output interpreter protocol appropriate for generation of second imaging requests understood by the Imation 952 output imaging device, which is already bound to an output driver component 24 having an output driver protocol appropriate for communication of the second imaging requests via a dual-port RAM hardware interface associated with the Imation 952 output imaging device. Thus, network interface component 14, including Toshiba-configured network driver and interpreter components 30, 32 would be unaffected by the modification.

The present invention's employment of inheritance conceptions of object-oriented programming provide for the advantage of reusability of network driver and interpreter components, as well as simplification in the creation of new network driver and interpreter components. Inheritance makes it possible to define new components by comparison with already developed components, which is known as differential programming. Common functionality within these components is reused, and therefore does not need to be redeveloped. Furthermore, any bug fixes and enhancements made to the base class are automatically propagated to the derived classes. In these ways, the present invention allows for the incorporation of new protocols into the software system in typically a shorter period of time, and utilizing a smaller number of resources, than is accomplished by the prior art.

Client-Server Hierarchy of the Components

As shown in FIG. 6, interface executive component 20 in one embodiment defines pipeline 26 according to a client-server architecture. In FIG. 6, an arrow pointing from a component A to a component B indicates that component A is a client component of server component B. The bi-directional arrows between network driver component 30 and network client 12 and between output driver component 24 and output imaging device 18 do not represent a client-server relationship, but rather the hardware/software interfaces of medical imaging system 10. As indicated by the arrows in FIG. 6, interface executive component 20 in one embodiment defines the client-server relationship of the software system such that: (1) interface executive component 20 is a client component of network executive component 14, output interpreter component 22 and output driver component 24; (2) network executive component 14 is a client component of network driver component 30 and network interpreter component 32; (3) network driver component 30 is a client component of network interpreter component 32; (4) network interpreter component 32 is a client component of output interpreter component 22; and (5) output interpreter component 22 is a client component of output driver component 24.

The client-server paradigm provides for seamless integration among the components of the present invention. The client component requests a service to be performed; the server is the resource that handles the client's request. More specifically, the client sends a message to a server to request that the server perform a task, such that the server responds to the client's request. Employing client-server relationships in the present invention allows for the advantage of increased maintainability above and beyond that provided by object-oriented programming precepts. Client-server computing recognizes that the separate components provided for by an object-oriented architecture need not all be executed from the same memory space. Thus, client-server computing promotes scalability: any of the components of the present invention may be replaced when the need to either grow or reduce processing for that component dictates, without significantly impacting the other components. As has been described, the components of the present invention reside within the same memory, be it on a card within the imaging device, or within the RAM of a computer to which the device is coupled. However, should the number of imaging devices with which the clients can communicate become relatively large, for example, the output interface components for each device could reside on a card within the device, while the remainder of the components could reside on a computer attached to the network. As a result of subscription to a client-server model, the present invention allows for relocation of individual components without great logical effect to the other components.

In the described client-server relationship of the present invention, output driver component 24 is purely a server component for output interpreter component 22, respectively. The output driver component 24 is responsible for low-level hardware requirements and is under control of the higher-level output interpreter component 22, respectively. The network interpreter component 32 is a client component of output interpreter component 22, which provides a set of functions by which the network interpreter component controls output imaging device 18. The output interpreter component 22 never initiates communication with network interpreter component 32, but rather provides services at the request of the network interpreter component. The network driver component 30 is a client component of network interpreter component 32, which communicates with the driver component 30 to receive and interpret the image information from a client to generate the first imaging requests. The network driver component 30 itself directly communicates with the clients, however, according to a particular protocol. Finally, every component 30, 32, 22 and 24 is a server component for interface executive component 20. Thus, interface executive component 20 ultimately controls the entire software system.

Communication Among the Components

Communication among the components of the present invention is carried out via the issuance of remote procedure calls (RPC's). A remote procedure call is a common communication mechanism often used in complex distributed software systems. A client component executes a particular function by issuing a remote procedure call to a corresponding server component. The remote procedure call handles all of the mechanisms necessary for inter-component communication. Each component is configured to provide services to a client component, but is unaware of which or how many components are actually using it as a server component. The server components simply perform the requests of the client components without exhibiting protocol-specific dependencies.

Employment of remote procedure calls allows the present invention to have advantages resultant of a concept called encapsulation. Encapsulation of a component means that other components only see the services or tasks that the component offers, with no visibility as to how these services and tasks are implemented. Thus, how a component implements its actions, and how its internal data is arranged, is "encapsulated" inside a procedural shell that mediates all access to the object via remote procedure calls. Only the component itself has visibility into its procedures and its data. The components of the present invention are, therefore, encapsulated units of functionality. Put another way, encapsulation enables information hiding and data abstraction. The actual method followed by a particular component is an implementation detail that is independent of how the data is used. Rather, the operations that can be performed on the encapsulated data are specified as part of the interface to the component, the remote procedure calls. Thus, the implementation details of the operations that manipulate the stored data can be changed without affecting the remote procedure calls. Along with the inheritance, the concept of encapsulation allows for the advantage of interchangeability of components within the present invention.

In one embodiment of the present invention, a remote procedure call is used to execute a function in the following manner. First, when a software process being performed by a client component needs to execute a particular function, the process simply calls the function by its identifier. A layer of software residing within the client component, commonly referred to as a "client stub," traps the function call. If the client stub determines that the software code necessary to perform the called function actually exists within another server component, the client stub creates a message enclosing any data passed with the function call, as well as any necessary packetizing and addressing. The client stub, in one embodiment, then sends the message to the server component via the real time operating system existing in the software system. The server module contains a layer of software code, known as the "server stub," that receives the message. The server stub strips apart the message and actually calls the correct local function with any data pulled from the message. The local function executes as if it were originally called locally, returning any information requested. The server stub creates a response based on the returned information, and sends the response to the client component via the operating system. Upon receipt of the response, the client stub pulls out the returned information and passes the information to the local software process that originally called the function. The local software process then continues unaware that any inter-module communication occurred.

Component Definitions of One Embodiment of the Present Invention

The following sub-sections provide details concerning the manner in which each base-class protocol can be implemented in an embodiment of medical imaging system 10 of FIG. 1, in accordance with the present invention. The sub-sections provide definitions and requirements of services provided by each of components 30, 32, 22 and 24, 14 represented for purposes of illustration in the C++ object-oriented programming language, with comments included where appropriate. Where C++ code is used below to illustrate the functionality of a particular component, the label "host" may be used to refer to network client 12 and the label "laser imager" or "LI" may be used to refer to output imaging device 18.

The Network Executive Base-Class Protocol

The network executive base-class protocol, in this embodiment, includes one remote procedure call that network executive component 14 is required to provide for its client component, interface executive component 20. The remote procedure call is described below in terms of the types of parameters handled and the functions performed.

| 1. | set_debug_level | Parameters: | Type: |
|---|---|---|---|
| | | debug level | DEBUG_LEVEL |
| | | Returns: | Type: |
| | | void | n/a |

The actual base class protocol for network executive component 14 can be defined in C++ code as follows:

```
class NETWORK_EXECUTIVE{
protected:
    LI_INTERFACE *li_handle;      // pointer to laser imager
                                  interface
    INT32 return_code;            // RC for OS operations
    DEBUG_LEVELS debug_level;     //Debug level for module
    IMAGER_CONFIG *im_cfg;        // imager/dicom configuration
                                  object
public:
    NETWORK_EXECUTIVE(LI_INTERFACE *,
    IMAGER_CONFIG*);
    virtual~NETWORK_EXECUTIVE(void);
    virtual void set_debug_level(DEBUG_LEVELS level);
    //set to new debug level
};
```

The base class protocol for a DICOM protocol-configured network executive component can be defined in C++ code as follows:

```
class DICOM_EXEC : public TaskVStack,
public NETWORK_EXECUTIVE{
    friend class EVENT_MGR;
private:
    void execute(void);
    Bool init_network(); //initialize DIMSE interface to net
    int connect(); //monitor network and wait for a SCU
    Bool checkHeapSpace(); //Check if enough heap for new SCU
    Bool checkHeapSpaceVer();
    //Check if enough heap for new verify-only SCU
public:
    int numConnections;
    int numConnectionsVer;
    Bool verification_only;
    int port;
    int network_socket;  // socket for executive to listen to network
    int assoc_sockfd;    // socket for new association
    DIMSE_nethandle netHandle;
        DICOM_EXEC(LI_INTERFACE *, IMAGER_CONFIG *);
    ~DICOM_EXEC(void);
    void async_handler(char, ID);
    //Asyncronous commands from Dicom Driver
    void set_debug_level(DEBUG_LEVELS level);
    //set to new debug level
};
```

In this example, the DICOM executive base class contains two remote procedure calls: set_debug_level() and async_handler(). The async_handler() RPC allows a DICOM_Driver to inform the DICOM_executive that it has completed a task and should be shut down.

The Network Driver Base-Class Protocol

The network driver base-class protocol, in this embodiment, may include two remote procedure calls: set_debug_level() and ni_event_handler(). The remote procedure calls are described below in terms of the types of parameters handled and the functions performed.

| 1. | set_debug_level | Parameters: | Type: |
|---|---|---|---|
| | | debug level | DEBUG_LEVEL |
| | | Returns: | Type: |
| | | void | n/a |
| 2. | ni_event_handler | Parameters: | Type: |
| | | Network Interpreter event | NI_EVENT |
| | | Returns: | Type: |
| | | void | n/a |

The ni_event-handler RPC receives asynchronous events from output imaging device 18 that are propagated via network interpreter component 32, output interpreter component 22 and output driver component 24.

As noted above, the network driver component 30 provides a mechanism for handling asynchronous events received from output imaging device 18. The events serve to inform network driver component 30 of a status change at output imaging device 18. Various events indicating the status of output imaging device 18 may include (1) NI_printer_update, which indicates that the output imaging device has changed it status, and (2) NI_print_job_update, which indicates an imaging job has changed its status. The function of the above status events is to avoid the need for the network client 12 to continuously poll output imaging device 18.

The actual base class protocol for the network driver component 30 can be defined in C++ as follows:

```
class NETWORK_DRIVER{
protected:
    INT32 return_code; // RC for OS operations
    ID assoc_socket; // socket descriptor for association
    IMAGER_CONFIG *imager_config; // Configuration information
    NETWORK_DRIVER(ID port, DEBUG_LEVELS,
    IMAGER_CONFIG *);
    virtual~NETWORK_DRIVER(void);
public:
    DEBUG_LEVELS debug_level; //Debug level for module
    virtual void set_debug_level(DEBUG_LEVELS level);
    //set to new debug level
    virtual void ni_event_handler(NI_EVENT,NI_async_data)=0;
};
```

The base class protocol for a DICOM protocol-configured network driver component may make use of a DD_NET_MONITOR object, which can be defined in C++ code as follows:

```
class DD_NET_MONITOR : public TaskVStack{
private:
    DICOM_DRIVER *master; //pointer to controlling object
    void execute(void); //main execution thread
public:
    DD_NET_MONITOR(DICOM_DRIVER *);
    ~DD_NET_MONITOR(void);
};
typedef enum {
    DD_PrinterStatusChange,
    DD_JobStatusChange
} DD_event
```

The DD_NET_MONITOR is an object internal to a DICOM_DRIVER object that implements the DICOM driver component. The DD_NET_MONITOR object continuously monitors the network for incoming messages and informs the DICOM_DRIVER object upon their arrival. The DICOM_DRIVER object then reads and processes the messages, passing any information to the DICOM_INTERPRETER object (network interpreter component 32) via RPC-based functions defined by the network interpreter component.

The base class protocol for a DICOM protocol-configured network driver component can be defined in C++ code as follows:

```
class DICOM_DRIVER : public TaskVStack,
public NETWORK_DRIVER {
    friend class DD_NET_MONITOR;
private:
    DD_NET_MONITOR network_monitor;
    //get messages from network
    //Association handling Methods and Parameters
    void associationServer(); //handle association
    void monitorNetwork();
    //continually accept and valid DICOM messages
    int processMessage(); //handle the received DICOM message
    //FilmSession Methods and Parameters
    void handleFilmSession(DIMSE_CmdSet cmdSet,
    DIMSE_MsgHandle msg);
    void fsNCreate(DIMSE_CmdSet cmdSet,
    DIMSE_MsgHandle msg);
    void fsNSet(DIMSE_CmdSet cmdSet, DIMSE_MsgHandle msg);
    void fsNAction(DIMSE_CmdSet cmdSet,
    DIMSE_MsgHandle msg);
    void fsNDelete(DIMSE_CmdSet cmdSet,
    DIMSE_MsgHandle msg);
    //FilmBox methods and parameters
    void handleFilmBox(DIMSE_CmdSet cmdSet,
    DIMSE_MsgHandle msg);
    void fbNCreate(DIMSE_CmdSet cmdSet,
    DIMSE_MsgHandle msg);
    void fbNSet(DIMSE_CmdSet cmdSet, DIMSE_MsgHandle msg);
    void fbNAction(DIMSE_CmdSet cmdSet,
    DIMSE_MsgHandle msg);
    void fbNDelete(DIMSE_CmdSet cmdSet,
    DIMSE_MsgHandle msg);
    //ImageBox methods and parameters
    void handleImageBox(DIMSE_CmdSet cmdSet,
    DIMSE_MsgHandle msg);
    void ibNSet(DIMSE_CmdSet cmdSet, DIMSE_MsgHandle msg);
    //Annotation Box methods and parameters
    void handleAnnoBox(DIMSE_CmdSet cmdSet,
    DIMSE_MsgHandle msg);
    void abNSet(DIMSE_CmdSet cmdSet, DIMSE_MsgHandle msg);
    //Printer methods and parameters
    void handlePrinter(DIMSE_CmdSet cmdSet);
    void prNGet(DIMSE_CmdSet cmdSet);
    //PrintJob methods and parameters
    void handlePrintJob(DIMSE_CmdSet cmdSet);
    void pjNGet(DIMSE_CmdSet cmdSet);
    //Misc functions
    void async_event_server();//server function called to process
    async events
public:
    DICOM_DRIVER(DICOM_EXEC *,ID,
    DICOM_INTERPRETER *,
    DIMSE_AssocHandle,DIMSE_SOPInfo *,
        DEBUG_LEVELS,IMAGER_CONFIG *);
    ~DICOM_DRIVER(void);
    void ni_event_handler(NI_EVENT,NI_async_data);
    };
```

In this example, the DICOM_DRIVER includes a large number of functions that operate on incoming DICOM messages. Most of the functions can be rather DICOM-specific and will be apparent to those skilled in the art in view of the DICOM standard. Each of these functions is internal and is closely tied to related DICOM DIMSE commands. In addition, the DICOM_DRIVER contains the RPC call that was specified in the network_driver base class: ni_event_handler(). The DICOM functions ultimately call network interpreter-specific functions that use the RPC mechanism.

The Network Interpreter Base-Class Protocol

The network interpreter base-class protocol, in this embodiment, includes remote procedure calls that network interpreter component 32 is required to provide for its client component, network executive component 14.

The actual base class protocol for network interpreter component 32 can be defined by the following C++ code in which the network interpreter is referred to as the "NETWORK INTERFACE":

```
//Define asyncronous events for network interface
typedef enum {
    NI_printer_update, // Announce that the LI's status has changed
    NI_print_job_update // Annouce that a print job's status
    has changed
} NIEVENT;
typedef union {
    int id; // ID of component that has changed its status
} NI_async_data;
typedef NETWORK_DRIVER *ND_PTR; // pointer to ND client
typedef void (NETWORK_DRIVER::*ND_METHOD_PTR)
    // pointer to client method
    (NI_EVENT, NI_async_data);
class NETWORK_INTERFACE{
protected:
    INT32 return_code; // RC for OS operations
    ID port_id; // initial network port
    Semaphore rpc_reply; // RPC response complete
    Semaphore rpc_free; // RPC mailbox free
    Semaphore event_reply; // async event received
    Semaphore event_free; // async event mailbox free
    Mailbox event_mbox; // event mailbox
    Mailbox rpc_mbox; // RPC mailbox
    ND_PTR driver; // driver module calling us
    ND_METHOD_PTR driver_async_handler;
    // pointer to async handler
    IMAGER_CONFIG *iconfig;
    // pointer to imager configuration object
    NETWORK_INTERFACE(ID, LI_INTERFACE *,
    DEBUG_LEVELS,
        IMAGER_CONFIG *);
    virtual ~NETWORK_INTERFACE(void);
    LI_INTERFACE *li_handle // Handle to LI interface
    DEBUG_LEVELS debug_level; // Debug level for module
    Param_Blk parameters; // Pointer to parameters
    LI_async_data li_async_data; // Data from LI events
public:
    virtual Bool li_event_handler(LI_INTERFACE_EVENT,
    LI_async_data);
    virtual void set_async_func(ND_PTR, ND_METHOD_PTR);
    virtual void set_debug_level(DEBUG_LEVELS level);
    //set new debug level
};
```

A base class protocol for a DICOM protocol-configured network interpreter component can be represented by the following C++ code:

```
// DICOM Interface Message type for RPCs
    typedef struct {
    DICOM_Command command;
    // DICOM command/event to execute
    DICOM_Response *response; // Pointer to response object
    DICOM_Data data;    // message data
} DICOM_Message;
class DICOM_INTERFACE : public TaskVStack, public
NETWORK_INTERFACE,
        public PrintServerInf, public SessionHandler {
private:
        DICOM_Message *message; // Pointer to RPC client message
        DICOM_Response *response; // Pointer to response object
        DICOM_Data *data; // message data
        INT32 return_code; // rpc return code
        PrinterStatus currentPrStatus;
        void execute(void);
        void send_rpc(DICOM_Message *);
        // Send msg to server thread
        void ack_rpc(void); // Acknowledge RPC completion
public:
        DICOM_INTERFACE
            (ID LI_INTERFACE *, DEBUG_LEVELS,
                IMAGER_CONFIG *);
        ~DICOM_INTERFACE(void);
        Bool li_event_handler
            (LI_INTERFACE_EVENT,LI_async_data);
        // Async event handler
};
class PrintServerInf : public BasePrintServer {
public:
        // Constructor - initialize the data members and establish
        // a connection with the PrintServer process.
        PrintServerInf(DICOM_INTERFACE*,IMAGER_CONFIG*);
        // Destructor - cleanup session and
        memory dynamically allocated
        ~PrintServerInf();
        // This method opens a film session at the PrintServer and
        // returns a pointer to a FilmSessionInf object.
        FilmSessionInf* openSession() { return openSession(String()); }
        FilmSessionInf* openSession(const String& origId);
        // This method closes the session at the PrintServer, resulting
        // in the deletion of all images previously stored in the session
        // and all the open film boxes.
        void closeSession();
        // This method gets the status information
        of a job specified by its id.
        bool getJobStatus(JobStatus& status, ID jobId);
        // The following methods allows a client to
        manipulate jobs on the
        // Print Server queue.
        // This method removes a job from the server's queue.
        bool cancel(ID jobId);
        // This method changes the priority of a job in server's queue.
        bool alterPriority(ID jobId, Priority p);
        // This method returns an object containing
        printer status information
        bool getPrinterStatus(PrinterStatus& status);
        // This method notifies the server to shutdown.
        void shutdown();
        void setHostName(const String& name);
        void setHostName(char* name);
protected:
        void connect();
        bool getPrintQueue(JobIdArray& jobs,
        ID sessionId, const String& origId);
        DICOM_INTERFACE* master;
        IMAGER_CONFIG *m_config;
private:
        FilmSessionInf* m_fs;
};
class SessionHandler {
        friend class DICOM_INTERFACE;
public:
        DICOM_INTERFACE* master;
        ID m_sessionId;
        ID m_fbId;
        ID m_imgId;
        LIST m_printJobs;
        Bool m_contrastTest;
        int m_images_acquired;
        LSVR_Status m_acquire_status;
        States m_state;
        String hostName;
        Bool m_contrastTestMode;
        PARAMETERS m_liparams;
        IMAGE *image_list[MAX_IMAGES_PER_PAGE];
        IMAGE image_list_store[MAX_IMAGES_PER_PAGE];
        IMAGE *raw_image_list[MAX_IMAGES_PER_PAGE];
        IMAGE raw_image_list_store
        [MAX_IMAGES_PER_PAGE];
        SessionHandler(DICOM_INTERFACE* m);
        virtual ~SessionHandler();
        ID getSessionId();
        ID getNextFilmBoxId() { return ++m_fbId; }
        ID getNextImageId() { return ++m_imgId; }
        Bool queryPrintJobs(ID jobId)
        { return m_printJobs.query(jobId); }
        void mapJobStatus(JobStatus* js);
        Bool handleContrastTestEvent(char* nid);
        void printContrastTest(ID image);
```

```
        LSVR_Status acquireAllImageMemory(int rows, int cols);
        void sessionClientHandler();
        void openSessionHandler();
        void closeSessionHandler();
        void newFilmBoxHandler();
        void printHandler();
        void imageAllocateHandler();
        void imageDataHandler();
        void deleteImageHandler();
        void filmAttrHandler();
        void imageAttrHandler();
        void associateImageHandler();
        void eraseImageHandler();
        void eraseAllImages();
        void deleteFilmBoxHandler();
        void getPrinterStatusHandler();
        void getPrintQueue();
        void getJobStatusHandler();
        void cancelJobHandler();
        void setPriorityHandler();
        void noImageHandler();
        void errorHandler();
        void cleanUpImages();
        void updateParameters(BaseFilmSession *fs, BaseFilmBox *fb);
};
```

The Output Interpreter Base-Class Protocol

The network interpreter component 32 interfaces with output interpreter component 22 via a set of imaging objects. The imaging objects serve as parameters for the remote procedure calls and contain all of the available information concerning the characteristics of output imaging device 18 and the imaging process. The network interpreter component 32 can use any part of the information and disregard the rest. There are six imaging object definitions including (1) a box object, (2) a format object, (3) an image object, (4) a test image object, 5) a string object, and 6) a variety of general imaging parameter objects.

A format object is used to describe an entire sheet of imaging media on which output imaging device 18 will form an image. The format object holds information relating to film type, film size, border color, border density, etc. The characteristics of the format object can be defined in C++ as follows:

```
class FORMAT {
public:
        FORMAT(FORMAT_ID);              // Constructor
        FORMAT(void);                   // Constructor
        void init(void);                // Initialize parameters
                                        to defaults
        FORMAT_ID id;                   // Format to which this
                                        box belongs
        TABLE bkgnd_color_table;        // Background/border color
                                        media table
        TABLE bkgnd_color_mixing_table; // Background/border color
                                        mixing table
        LEVEL bw_border_level;          // B&W border level
        COLOR color_brd_level;          // Border Color levels
        LEVEL bw_density_max;           // B&W maximum density
        FILM_TYPE film_type;            // Type of film to use
        FILM_SIZE film_size;              // Size of film to use
};
```

A box is a rectangular area of the film sheet designated to hold an image. The box has many characteristics including location, size, contrast, color, etc. The box definitions are associated with a particular format. That is, several boxes are used in conjunction with a particular format. The following C++ code describes the box object and its characteristics:

```
class BOX {
public:
        BOX(BOX_ID id,                  // Constructor
        FORMAT_ID id);
        BOX(void);                      // Constructor
        void init(void);                // Initialize parameters
                                        to defaults
        BOX_ID id;                      // Box id #
        FORMAT_ID format_id             // Format the box
        TABLE beta_x1;                  // Horizontal axis beta pass 1
        TABLE beta_y1;                  // vertical axis beta pass 1
        TABLE beta_x2;                  // Horizontal axis beta pass 2
        TABLE beta_y2;                  // Vertical axis beta pass 2
        TABLE color_media_table;        // Color media table to use
        TABLE contrast_table;           // B&W contrast table to use
        TABLE color_contrast_table;     // Color contrast table to use
        TABLE color_mixing_table;       // Color mixing table to use
        FRAME frame;                    // Frame to use around border
        LOCATION x_location;            // Horizontal pixel location
        LOCATION y_location;            // Vertical pixel location
        Switch mirroring;               // Turn mirroring on and off
        Switch rotation;                // Turn rotation on and off
        OUTPUT_SIZE output_size_x1;     // X output size pass 1
        OUTPUT_SIZE output_size_y1;     // Y output size pass 1
        OUTPUT_SIZE output_size_x2;     // X output size pass 2
        OUTPUT_SIZE output_size_y2;     // Y output size pass 2
        OFFSET window_x_offset;         // Window X offset from corner
        OFFSET window_y_offset;         // Window Y offset from corner
        LENGTH window_x_length;         // Horizontal length of window
        LENGTH window_y_Length;         // Vertical length of window
        };
```

An image is represented by image data containing digital image values. The image data is stored in an image memory associated with output imaging device 18. The image object is used to associate certain characteristics with the image. As indicated by the above code, the characteristics may include pixel length, pixel width, pixel depth, color format, etc. When printing, an image is used to fill the boxes defined for the format that is to be used. The following C++ code describes the image object and its characteristics:

```
class IMAGE {
public:
        IMAGE(void);                    // constructor
        IMAGE(IMAGE_ID id);             // constructor
        void init(void);                // Initialize parameters to defaults
        IMAGE_ID id;                    // Identification Number
        COLOR_FORMAT mode;              // color image format
        LENGTH x_length;                // horizontal image length in pixels
        LENGTH y_length;                // vertical image length in lines
        DEPTH image_depth;              // depth of image 8–12 bits
        DURATION timeout;               // acquire timeout for this image
        Switch permanent;               // image will be held for a while
};
```

A test image object is used to symbolize images used for testing purposes. The images are software generated and have different attributes than an image. The following C++ code describes the test image object and its characteristics:

```
class TEST_IMAGE {
public:
        TEST_IMAGE(void);               // constructor
        TEST_IMAGE                      // constructor
        (IMAGE_ID id);
        void init(void);                // Initialize parameters to defaults
        IMAGE_ID id                     // Identification Number
        COLOR_FORMAT mode;              // color image format
```

```
               -continued
LENGTH x_length;        // horizontal image length in
 pixels
LENGTH y_length;        // vertical image length in lines
DEPTH image_depth;      // depth of image 8–12 bits
DURATION timeout;       // acquire timeout for this image
TEST_IMAGE_TYPE         // type of test pattern
 image_type;
LEVEL red_density;      // Constant density - red density;
LEVEL green_density;    // Constant density - green density;
LEVEL blue_density;     // Constant density - blue density;
};
```

A string object is used to hold ASCII text in the image memory. The string object also allows the use of parameters such as length, intensity, type, etc. The following C++ code describes the string object and its characteristics:

```
class STRING {
public:
     STRING(void);                    // constructor
     STRING(IMAGE_ID id);             // constructor
     void init(void);                 // Initialize parameters to
                                      defaults
     STRING_ID id;                    // id of string
     TEXT_TYPE type;                  // Type of the text
     char *text;                      // string
     LEVEL bw_foregnd_intensity;      // B&W forground intensity
     LEVEL bw_backgnd_intensity;      // B&W forground intensity
     COLOR color_foregnd_intensity;   // Color foreground intensities
     COLOR color_backgnd_intensity;   // Color background
                                      intensities
     LENGTH width;                    // width of string
     LENGTH lead;                     // # of blank lines between
                                      ASCII lines
};
```

The general parameters object is used to hold all process configuration parameters. This object can be used to set the parameters in the laser imager, or to read the current settings of the parameters. Examples of some parameters are default beta tables, default color contrast, default destination, default film size and type, etc. A few parameters are read-only, and thus cannot be set, such as the amount of memory available, the current software revision, the total prints queued, etc. The following C++ code describes the general parameter object and its characteristics.

```
class PARAMETERS {
public:
     PARAMETERS(void);          // Constructor
     void set_defaults(void);   // Initialize to defaults
     DURATION acq_timeout;      // Acquisition timeout
                                1..65535 seconds
     TABLE def_beta_x1;         // Default horizontal axis
                                beta pass 1
     TABLE def_beta_y1;         // Default vertical axis
                                beta pass 1
     TABLE def_beta_x2;         // Default horizontal axis
                                beta pass 2
     TABLE def_beta_y2;         // Default vertical axis
                                beta pass 2
     LEVEL def_bw_border;       // Default B&W Border level
     COLOR def_color_border;    // Default color border level
     COLOR_FORMAT def_cformat;  // Default acquisition
                                image format
     TABLE def_bw_contrast;     // Default contrast table while
                                in B&W
     TABLE def_color_contrast;  // Default contrast table while
                                in color
```

```
               -continued
     TABLE def_color_mix;       // Default mixing table while
                                in color
     LEVEL def_max_density;     // Default maximum density
                                value
     DEPTH def_depth;           // Default bits per pixel
     DESTINATION def_destination; // Default destination
                                for print images
     LEVEL def_bw_dmax;         // Default B&W maximum
                                density value.
     IMAGE_TYPE def_image_type; // Default acceptable image type
     FILM_TYPE def_film_type;   // Default media type
     FILM_SIZE def_film_size;   // Default media size
     LENGTH def_image_xsize;    // Default width of image
                                in pixels
     LENGTH def_image_size;     // Default length of image
                                in lines
     Switch fixed_formatting;   // Switch for fixed formatting
     FIXED_FORMAT fixed_format; // Fixed format number
/Read only parameters/
     long int fixed_image_pattern; // Image acquisition pattern
     MEMORY memory;             // Memory status structure
     OP_MODE op_mode;           // Operational mode
     RELEASE revision;          // Current revision
     SYSTEM system;             // Imaging system of the
                                Laser Imager
     int total_queued;          // Total prints queued in
                                the system
     int total_completed;       // Total prints completed in
                                current jobs
     int total_failed;          // Total prints failed in
                                current jobs
};
```

One of the major responsibilities of output interpreter component 22 is to relay the status of the output imaging device 18 to the client component, network intrepreter component 32. The status relay process has two steps. When output interpreter component 22 notes a status change in output imaging device 18, the event handler in the client component is called directly by the output interpreter component. The event handler is passed a status event. The possible status events include (1) the FP_status_change, (2) the PR_status_change, (3) the IMS_status_change, (4) the JOB_status_change, and (5) the XFR_status_change. The output interpreter component 24 notifies the client, network interpreter component 22, of the above status changes, so that the network interpreter component does not need to continuously poll the laser imager.

It is the responsibility of the client, network interpreter component 32, to either ignore the status change or request further information. All status information is contained within five status objects. There is status object for the film processor, the printer, the image management system, jobs, and background jobs (transfers). Each status object has a status field which can be easily checked to see if warnings or errors exist. If warnings or errors exist, further examination of the warnings structure or the error structure can be done. Again, the client can choose to use only the information it needs. The following C++ code shows the definition for each of the status objects and the structures they contain:

```
/**Film Processor Status object typedefs and class definition **/
class Film_Processor {
public:
    Film_Processor(void);           // Constructor
    void clear(void);               // clears status object
    int id;                         // Id
    int Warming time;               // Time till warm
    FP_Type type;                   // Film Processor Type
    FP_Status status;               // Film Processor status
    FP_Warnings warnings;           // current warnings in Film Processor
    FP_Errors errors;               // current errors in Film Processor
};
typedef enum {
    Antares_FP,                     // Antares film processor.
    LT_SE154_FP,                    // LT film processor.
    No_FP,                          // No film processor connected.
    Spectrum_FP                     // Spectrum film processor.
} FP_Type;
typedef struct {
    unsigned Busy     : 1;          // Processor is in clean-up or busy with media
    unsigned NoFP     : 1;          // No film processor docked
    unsigned OpenLoop : 1;          // Not doing calibration
    unsigned Ready    : 1;          // Ready to process film
    unsigned Warming  : 1;          // Warming up
    unsigned Warnings: 1;           // Warnings exist
    unsigned Errors   : 1;          // Errors exist
} FP_Status;
typedef struct {
    unsigned CheckChem : 1;         // Chemistry is getting bad.
    unsigned Generic   : 1;         // Miscellaneous
    unsigned HiOvf     : 1;         // One or more overflow tanks is getting high
    unsigned LoChem    : 1;         // One or more chemistry tanks is getting low
} FP_Warnings;
typedef struct {
    unsigned FPDown    : 1;         // Processor is not operational
    unsigned FullOvf : 1;           // One or more overflow tanks are full
    unsigned Generic : 1;           // Miscellaneous
    unsigned MediaJam : 1;          // Media jammed in the film processor
    unsigned OutChem : 1;           // One or more film chemistry tanks are empty
} FP_Errors;
/Image Managment System Status object typedefs and class definition/
class Image_Mgmnt_System {
public:
    Image_Mgmnt_System(void);       // Constructor
    void clear(void);               // clears status object
    IMS_status status;              // Image Management System status
    IMS_errors errors;              // current errors in Image Management System
};
typedef struct {
    unsigned PowerUp : 1;           // First status since it has been powered up.
    unsigned Errors : 1;            // Errors exist in the system
} IMS_status;
typedef struct {
    unsigned Badconfig    : 1;      // IMS is configured improperly
    unsigned BadTblEprom : 1;       // Table EPROMS have an incorrect checksum
    unsigned IMNVRamErr : 1;        // Non volatile ram error in an input module
    unsigned IMSDown     : 1;       // IMS is not operational.
    unsigned OMNVRamErr1 : 1;       // Non volatile ram error in output module 1
    unsigned OMNVRamErr 2: 1;       // Non volatile ram error in output module 2
    unsigned MemBlkErr : 1;         // 10% or more of image memory is bad
} IMS_errors;
/**   Printer Status object typedefs and class definition     **/
class Printer {
public:
    Printer(void);                  // Constructor
    void clear(void);               // clears status object
    int id;                         // Printer Id
    int SheetsRemaining;            // # of sheets left
    FILM_TYPE MediaType;            // Type of film loaded
    FILM_SIZE MediaSize;            // Size of film loaded
    int ImgPixels;                  // # of imageable pixels
    int ImgLines;                   // # of imageable lines in media
    Quality quality;                        // Current quality condition
    PR_type type;                   // Printer Type
    PR_status status;               // Printer status flags
    PR_warnings warnings;           // current warnings in Printer
    PR_errors errors;               // current errors in Printer
};
typedef struct {
```

-continued

```
        unsigned Warnings: 1;           // Warnings exist in the system
        unsigned Errors : 1;            // Errors exist in the system
} PR_status;
typedef enum {
        Draft,
        Photo
} Quality;
typedef enum {
        Spectrum_PR,                    // Spectrum printer.
        Antares_PR,                     // Antares printer.
        LT_SE154_PR,                    // LT printer.
        No_PR,                          // No printer connected
        XL_PR                           // XL (Roadrunner) printer
} PR_type;
typedef struct {
        unsigned MediaLow    : 1;       // Media is low (less than 20 sheets).
        unsigned Busy        : 1;       // The printer has a transient problem.
        unsigned PrCalib     : 1;       // Printer is generating a calibration sheet.
} PR_warnings;
typedef struct {
        unsigned BadCass     : 1;       // Media cassette is inoperable.
        unsigned CassErr     : 1;       // Cassette error occurred.
        unsigned CassJam     : 1;       // Media jam at cassette.
        unsigned CoverOpen   : 1;       // One of the covers is open.
        unsigned ExpJam      : 1;       // Media jam at exposure point.
        unsigned MediaOut    : 1;       // No media in printer.
        unsigned NoCass      : 1;       // No media cassette in printer.
        unsigned PanelErr    : 1;       // Printer LCD panel in non operable
        unsigned PrDown      : 1;       // Printer is not operational
        unsigned RecMagFull  : 1;       // The Rec Magazine is full and needs to be emptied.
        unsigned RecMagMiss  : 1;       // The Receive Magazine is not in the printer.
        unsigned ToExpJam    : 1;       // Media jam transporting to exposure point.
        unsigned ToProcJam   : 1;       // Media jam transporting to film processor.
} PR_errors;
/**     Job Status object typedefs and class definition      **/
class Job {
public:
        Job(void);                      // Constructor
        void clear(void);               // clears status object
        int id;                         // JOB Id
        int PrintsComplete;             // # prints printed properly
        int PrintsFailed;               // # prints printed improperly
        int PrintsQueued;               // # prints waiting to be printed
        int FilmsComplete;              // # sheets printed properly
        int FilmsFailed;                        // # sheets printed improperly
        int FilmsQueued;                // # sheets waiting to be printed
        JOB_status status;              // JOB status
        JOB_errors errors;              // current errors in JOB
};
typedef struct {
        unsigned Done      : 1;         // Job is complete
        unsigned Killed : 1;            // Job was killed
        unsigned Stopped : 1;           // Job was stopped
        unsigned Wait    :              // Print is in print queue
        unsigned Errors : 1;            // Job has errors
} JOB_status
typedef struct {
        unsigned Aborted     : 1;       // Abort command issued
        unsigned BadBand     : 1;       // Images not contained in a single band
        unsigned BadMedia    : 1;       // Media not available.
        unsigned BadTable    : 1;       // Invalid table specified
        unsigned CrossPrtErr : 1;       // Illegal configuration'
        unsigned FPErr    : 1;          // Film processor has failed.
        unsigned ImgAbut     : 1;       // Images illegally abut each other
        unsigned IMSErr      : 1;       // Images illegally abut each other
        unsigned LinePixelErr : 1;      // Too many pixels
        unsigned MaxBadCnt   : 1;       // Two identical errors
        unsigned MaxBandImg : 1;        // max images per band
        unsigned MaxHorImg    : 1;      // max horizontal images
        unsigned MinBand     : 1;       // Fewer than min lines per band
        unsigned Parity   : 1;          // Parity error within an image
        unsigned PrErr    : 1;          // Printer has failed
        unsigned RecMagErr   : 1;       // Receive Magazine missing or full.
        unsigned WrongQual   : 1;       // Quality not available
} JOB_errors;
/**    Transfer Job Status object typedefs and class definition    **/
class Xfr {
public:
        Xfr(void);                      // Constructor
```

-continued

```
        void clear(void);          // clears status object
        int id;                    // JOB Id
        Length X_size;             // Horizontal image size (if job complete)
        Length Y_size;             // Vertical image size (if job complete)
        XFR_status status;         // JOB status
        XFR_errors errors;         // current errors in JOB
};
typedef int Length;
typedef struct {
        unsigned Wait : 1;         // Job is in queue
        unsigned Done : 1;         // Job is complete
        unsigned Killed : 1;       // Job was killed
        unsigned Errors: 1;        // Job has errors
} XFR_status
typedef struct {
        unsigned Aborted    : 1;   // Abort command issued
        unsigned AcqErr     : 1;   // Acquisition error.
        unsigned BadDepth   : 1;   // The depth specified cannot be set.
        unsigned BadMode    : 1;   // Incorrect current mode.
        unsigned ConnectErr : 1;   // Connection error
        unsigned EibParamErr: 1;   // Bad parameter in NVRAM
        unsigned EibSrcErr  : 1;   // Bad source value in NVRAM
        unsigned EibTranErr : 1;   // Error while translating EIB parameters
        unsigned FifoErr    : 1;   // FIFO overflow
        unsigned MemBoundErr: 1;   // Outside boundary of available memory
        unsigned MemErr     : 1;   // Memory error during store
        unsigned MemFull    : 1;   // Image memory is full
        unsigned NVRamErr   : 1;   // Misc error with NVRAM
        unsigned ParityErr  : 1;   // Parity error
        unsigned ResErr     : 1;   // store to reserved memory failed
        unsigned SetUpErr   : 1;   // Configuration error
        unsigned SizeErr    : 1;   // Image size error
        unsigned TimeOut    : 1;   // System timed out during image store
} XFR_errors
```

The output interpreter component 24, in this embodiment, provides fifteen types of remote procedure calls. With the use of the above described imaging objects and the remote procedure calls, the client can fully operate output imaging device 18. Note that all of the parameters contained in the imaging objects described above are initialized to an "unassigned value". If the parameter is not changed by the client, the output interpreter component 24 will ignore it. This feature allows the client to use only the parameters that it needs. Each of the remote procedure calls provided by output interpreter component 24 is described below. Unless otherwise indicated, the return for each of the following remote procedure calls is a Laser Imager Response Object of type LI_response, which will be further described later in this disclosure.

```
    1.  Media Print RPCs
        a.  print       Parameters:       Type:
                        copies (opt)      int
```

The above RPC initiates a general print from a laser imager functioning as output imaging device 18. The above RPC is designed to be used with fixed-formatting. The format is a currently selected fixed format. Copies is an optional parameter indicating the number of copies to produce. The images that have been acquired since the last print will be used for the print.

```
        b.  print       Parameters:       Type:
                        format            int
```

-continued

```
                        image list        LIST
                        copies (opt)      int
                        density (opt)     int
                        destination (opt) DESTINATION
```

The above RPC initiates a print from the laser imager. Format is the format ID to use. Image list indicates which images to use to fill the format. Copies is an optional parameter indicating the number of copies to produce. Density is an optional integer which is used when a density test patch is desired. The integer value corresponds to an image ID. Destination is an optional parameter that defines a destination for the output rather than the default.

```
        c.  print_test  Parameters:       Type:
                        format            int
                        image list        LIST
                        dens_id           IMAGE_ID
                        copies (opt)      int
                        destination (opt) DESTINATION
```

The above RPC initiates a print from the laser imager. Format is the format ID to use. Image list indicates which images to use to fill the format. Dens_id is an integer that represents the image id of a density test patch. Copies is an optional parameter indicating the number of copies to produce. Destination is an optional parameter which defines a destination for the output rather than the default.

| | | | |
|---|---|---|---|
| d. | abort | Parameters: job ID | Type: JOB_ID |

The above RPC aborts a job having the corresponding id.

| | | | |
|---|---|---|---|
| e. | abort | Parameters: none | Type: n/a |

The above RPC aborts all jobs that have been started.

2. Formatting RPCs

| | | | |
|---|---|---|---|
| a. | define | Parameters: format object | Type: FORMAT |

The above RPC defines a format with the exact parameters as found in the format object. All parameters equal to NOT_ASSIGNED are not included in the definition.

| | | | |
|---|---|---|---|
| b. | define | Parameters: box object | Type: BOX |

The above RPC defines a box with the exact parameters as found in the box object. All parameters equal to NOT_ASSIGNED are not included in the definition.

| | | | |
|---|---|---|---|
| c. | modify | Parameters: box object | Type: BOX |

The above RPC modifies the box that matches the id specified in the box object. All parameters equal to NOT_ASSIGNED in the box object are not modified.

| | | | |
|---|---|---|---|
| d. | modify | Parameters: box object x_shift y_shift | Type: BOX LENGTH LENGTH |

The above RPC modifies the box that matches the id specified in the box object. The location of the box is shifted by the amounts specified in x_shift and y_shift. All parameters equal to NOT_ASSIGNED in the box object are not modified.

| | | | |
|---|---|---|---|
| e. | modify | Parameters: format object | Type: FORMAT |

The above RPC modifies the format that matches the id specified in the box object. All parameters equal to NOT_ASSIGNED in the format object are not modified.

| | | | |
|---|---|---|---|
| f. | remove | Parameters: none | Type: n/a |

The above RPC deletes the last image acquired.

| | | | |
|---|---|---|---|
| g. | remove | Parameters: box object def (opt) all (opt) | Type: BOX Bool Bool |

The above RPC deletes the box with an id matching that of the received BOX object. DEF is an optional parameter that when set to TRUE causes the job to be deferred and processed in the background. If not received, DEF is set to FALSE. ALL is an optional parameter that when set to TRUE causes all defined boxes to be deleted. If not received, ALL is set to FALSE.

| | | | |
|---|---|---|---|
| h. | remove | Parameters: format object def (opt) all (opt) | Type: FORMAT Bool Bool |

The above RPC deletes the format with id matching that of the received FORMAT object. DEF is an optional parameter that when set to TRUE causes the job to be deferred and processed in the background. If not received, DEF is set to FALSE. ALL is an optional parameter that when set to TRUE causes all defined formats to be deleted. If not received, ALL is set to FALSE.

| | | | |
|---|---|---|---|
| i. | remove | Parameters: image object def (opt) all (opt) | Type: IMAGE Bool Bool |

The above RPC deletes the image with id matching that of the received IMAGE object. DEF is an optional parameter that when set to TRUE causes the job to be deferred and processed in the background. If not received, DEF is set to FALSE. ALL is an optional parameter that when set to TRUE causes all defined images to be deleted. If not received, ALL is set to FALSE.

| | | | |
|---|---|---|---|
| j. | remove_all | Parameters: def (opt) | Type: Bool |

The above RPC deletes all images, boxes, formats and tables defined in the laser imager. DEF is an optional parameter that when set to TRUE causes the job to be deferred and processed in the background. If not received, DEF is set to FALSE.

| | | | |
|---|---|---|---|
| h. | remove_fixed_images | Parameters: none | Type: n/a |

The above RPC deletes all images stored via fixed format store RPCs.

| 3. Image Manipulation RPCs | | |
|---|---|---|
| a. store | Parameters: none | Type: n/a |

This remote procedure call is strictly used with fixed formatting. This remote procedure call acquires the next image into the next available fixed image location. The locations range from 1 to N where N is the format specific.

| b. store | Parameters: id | Type: FIXED_ID |
|---|---|---|

This remote procedure call is strictly used with fixed formatting. This remote procedure call acquires the next image into the location specified by id. The locations range from 1 to N were N is the format specific.

| c. store | Parameters: image | Type: IMAGE |
|---|---|---|

The above RPC acquires the next image. The return information regarding image size is placed in LI_response.

| d. store | Parameters: image | Type: TEST_IMAGE |
|---|---|---|

The above RPC acquires the next image as a test pattern. The return information regarding image size is placed in LI_response.

| e. store | Parameters: string | Type: STRING |
|---|---|---|

The above RPC stores the text and the id in the STRING object. This allows the client component to recall the text at any time via the id. The return information regarding string size is placed in LI_response.

| f. transfer | Parameters: image | Type: IMAGE |
|---|---|---|

The above RPC transfers the next image as a background job. The return information regarding image size is available when image transfer is complete.

| g. reserve | Parameters: image | Type: IMAGE |
|---|---|---|

The above RPC allocates enough image memory to hold the image described by the IMAGE object.

| 4. Process Configuration/Status RPC | | |
|---|---|---|
| a. set | Parameters: parameter object | Type: PARAMETER |

The above RPC sets the imaging parameters for the laser imager. All parameters set to NOT_ASSIGNED will be left unchanged.

| 5. Status RPCs | | |
|---|---|---|
| a. show | Parameters: parameter object | Type: *PARAMETER |

The above RPC retrieves the imaging parameters for the laser imager.

| b. show_fixed | Parameters: parameter object | Type: *PARAMETER |
|---|---|---|

The above RPC retrieves the fixed formatting imaging parameters for the laser imager. All other members in the parameter object are left unchanged. All other members in the parameter object are left unchanged.

| c. show_mem | Parameters: parameter object | Type: *PARAMETER |
|---|---|---|

The above RPC retrieves the memory conditions of the laser imager.

| d. show | Parameters: image object | Type: *IMAGE |
|---|---|---|

The above RPC retrieves the length and width of the image with id matching the id given in the image object. All image information is placed in the image object.

| e. show | Parameters: printer object | Type: *PRINTER |
|---|---|---|

The above RPC retrieves the status of the printer with id matching the id given in the printer object. All printer information is placed in the printer object.

| f. show | Parameters: job object | Type: *JOB |
|---|---|---|

The above RPC retrieves the status of the job with id matching the id given in the job object. All job information is placed in the job object.

| | | Parameters: | Type: |
|---|---|---|---|
| g. | show | printer object | *XFR |

The above RPC retrieves the status of the transfer job with id matching the id given in the transfer job object. All transfer job information is placed in the transfer job object.

| | | Parameters: | Type: |
|---|---|---|---|
| h. | show_formats | string | *char |

The above RPC retrieves a string of id's of the defined formats.

| | | Parameters: | Type: |
|---|---|---|---|
| i. | show_images | string | *char |

The above RPC retrieves a string of id's of the acquired images.

| | | Parameters: | Type: |
|---|---|---|---|
| j. | show_con_tables | string | *char |

The above RPC retrieves a string of id's of the defined contrast tables.

| | | Parameters: | Type: |
|---|---|---|---|
| k. | show_con_tables | string | *char |

The above RPC retrieves a string of id's of the defined color contrast tables.

| | | Parameters: | Type: |
|---|---|---|---|
| 1. | set_debug_level | debug level | DEBUG_LEVEL |
| | | Returns: | Type: |
| | | Driver return code | DRIVER_RC |

The above RPC allows the client component to set the debug level of network interpreter component 32. The debug levels are NO_DEBUG, LOW_DEBUG, MEDIUM_DEBUG, and HIGH_DEBUG. This parameter affects the information displayed during debugging.

One advantage of the interface to output interpreter component 22 is that every remote procedure call returns a similar object. This object is called, most appropriately, the laser imager response object, as indicated above. Within the laser imager response object is a plethora of information regarding the result of the remote procedure call. However, the client may choose to examine only the information relevant to its needs. The laser imager response object has three main fields. The first is a simple boolean value entitled success. The boolean value reflects whether the request associated with the remote procedure call was accomplished or whether it failed. This information may satisfy the needs of most client components. The second field, success_data, returns any values that the client component expects if the command was successful. Normally, there will not be any information for a successful command. However, one example of information returned for a successful command would be the image size that is returned after a successful store image command. The third field, errors, is used to explain why the remote procedure call failed. This field is actually a comprehensive bit field of errors that the laser imager may incur. Again, this field is only valid if success is false.

The C++ code listed below describes the laser imager response object. The class defines the response received from the laser imager after a command has been issued. If the command executed successfully, the SUCCESS flag is set to TRUE. Any data that is received upon a successful completion will be stored in Success_Data. If the command failed, the SUCCESS flag is set to FALSE. The cause of the failure is stored in the Failures structure

```
class LI_response {
    friend SS_EXECUTIVE;
    Command cmd;                    // SS command
public:
    LI_response(void);              // constructor
    Bool success;                   // Command executed to completion
    Success_Data success_data;          // Only valid upon successful completion
    Failures errors;                // If command failed, errors causing failure
};
typedef struct {
    unsigned AcqErr     : 1;        // Acquistion Error
    unsigned AcqLockout : 1;    // Acquistion never attempted, not available
    unsigned BadBoxId   : 1;    // Box ID does not exists for modification
    unsigned BadDepth   : 1;    // Pixel depth error
    unsigned BadFmtId   : 1;    // Format ID does not exist
    unsigned BadPar     : 1;        // Bad Parameter
    unsigned BadCConTbl : 1;    // Bad Color Contrast Table
    unsigned BadCMediaTbl : 1;  // Bad Color Media Table
    unsigned BadConTbl  : 1;    // Bad Contrast Table
    unsigned BadCMixTbl : 1;    // Bad Color Mixing Table
    unsigned BadDensTest : 1;   // Image is not a valid density test patch
    unsigned BadDest    : 1;        // Invalid destination
    unsigned BadImgId   : 1;    // Image was not found
    unsigned BadJobId   : 1;    // Job was not found
    unsigned BadMedia   : 1;    // Media type correct
    unsigned BadMode    : 1;    // Incorrect input mode (color/b&w)
```

-continued

```
    unsigned BoxInUse   : 1       // Box is currently being used
    unsigned Busy       : 1;      // Module is aiready doing an image transfer
    unsigned CConInUse  : 1;      // Color Contrast table currently being used
    unsigned ConInUse   : 1;      // Contrast table is currently being used
    unsigned ConnectErr : 1;      // Hardware connection problem
    unsigned EibParamErr : 1;     // EIB parameter error
    unsigned EibSrcErr  : 1;      // Invalid EIB source
    unsigned EibTranErr : 1;      // EIB transfer parameters invalid
    unsigned Empty      : 1;      // Mbox is currently empty
    unsigned FifoErr    : 1;      // FIFO overflow
    unsigned FmtFull    : 1;      // would be more than 255 boxes in a format
    unsigned FmtInUse   : 1;      // Format currently being used
    unsigned FmtOvrLap  : 1;      // The boxes in this format overlap
    unsigned FmtOffSheet : 1;     // box in this format will not fit on media
    unsigned FmtTMCon         : 1;    // Too many contrast tables in this format
    unsigned FmtTMCCon        : 1;    // Too many color cont tables in this format
    unsigned FmtTMCMix : 1;           // Too many color mix tables in this format
    unsigned FmtTMCMedia : 1;         // Too many color med. tables in this format
    unsigned FmtTMImgs        : 1;    // Too many images specified in image list
    unsigned Full       : 1;      // MBOX is full
    unsigned InModInUse : 1;      // Input Module is currently being used
    unsigned ImgInuse   : 1;      // Image is currently being used
    unsigned ImgInvalid : 1;      // Image has not been fully stored yet
    unsigned JobDone    : 1;      // Job has already terminated
    unsigned MagErr     : 1;      // Magnification error
    unsigned MaxFmts    : 1;      // There would be more than 255 formats
    unsigned MaxJobs    : 1;      // Would exceed max # concurrent jobs
    unsigned MemBoundErr : 1;     // Invalid image memory address
    unsigned MemErr     : 1;      // Memory error occured during store
    unsigned MemFull    : 1;      // Image Memory is full
    unsigned MissPar    : 1;      // Missing Parameter
    unsigned MovErr     : 1;      // Move would cause box location to become neg.
    unsigned NoMem      : 1;      // Not enough memory to execute command
    unsigned NVRamErr   : 1;      // Problem with the Non-Volatile memory
unsigned ParityErr  1:            // Hardware parity error
    unsigned PassErr    : 1;      // Double pass required, single pass module
    unsigned QueueFull  : 1;      // Print Queue full. No more jobs possible.
    unsigned ResErr     : 1;      // Image size did not match reserved memory
    unsigned SetUpErr   : 1;      // Request does not match system configuration
    unsigned SizeErr    : 1;      // Size in Img Header does not match image size
    unsigned StoErr     : 1;      // Video or Digital signal error during acquisition
    unsigned TimeOut    : 1;      // Image acquistion could not be completed
    unsigned TooLong    : 1;      // Message is too long to fit in the mbox
    unsigned Unkillable : 1;      // Job(s) cannot be killed
    unsigned UnknownCmd : 1;      // Unknown command issued
    unsigned WinErr     : 1;      // Window specified is incorrect size
} Failures;
```

The following structure holds data that input imaging device 18 (the laser imager) returns if the command executes correctly. Thus, this data is only valid if no errors occurred during execution.

```
typedef struct {
    ID id;                   // Place holder for a return ID
    LENGTH  x_size;          // Place holder for an Image size
    LENGTH  y_size;          // Place holder for an Image size
```

```
    LIST list;               // Place holder for an ID list
} Success_Data;
```

The actual base class for output interpreter component 24 can be defined in C++ as follows:

```
class LI_INTERFACE {
public:
    LI_INTERFACE(PORT_ID new_id, OUTPUT_INTERFACE *p);//constructor
    ~LI_INTERFACE(void);
    INT32 return_code;              // RC for OS operations
    DRIVER_RC out_driver_rc;        // RC from output driver
    DEBUG_LEVELS debug_level;       // Debug level for module
    Semaphore rpc_reply;            // RPC response complete
    Semaphore rpc_free;             // RPC mailbox free
    Semaphore event_reply;          // async event received
    Semaphore event_free;           // async event mailbox free
```

-continued

```
    PORT_ID exec_id;
    Mailbox rpc_mbox;              // RPC mailbox
    Mailbox event_mbox;            // event mailbox
    OUTPUT_INTERFACE *output_handle;
    FE_PTR client;                 // client module using us
    FE_METHOD_PTR client_async_handler;   // pointer to async handler
    virtual Bool output_ev_handler(enum IO_EVENT event) =0
                                                //asynch event handler
    virtual void set_async_func(FE_PTR,FE_METHOD_PTR)=0;
                                                //set ptr to FE handler
    /*** Laser Imager Client Interface ***/
    // Basic Transparent Command
    virtual LI_response send(char *);       //send generic text
    virtual LI_response receive(char *);    //receive generic text
    // Print Commands
    virtual LI_response print(int copies=1)=0; //Fixed format print
    virtual LI_response print(FORMAT_ID id,LIST *images,
            int copies=1,DESTINATION d=Film_Processor_1)=0;
        virtual LI_response print_test(FORMAT_ID id,LIST *images,
            IMAGE_ID dens_id int copies=1,
            DESTINATION d=Film_Processor_1)=0;
    virtual LI_response abort(JOB_ID id)=0;
    virtual LI_response abort(void)=0;      //Abort all jobs
    // Formatting Commands
    virtual LI_response define(BOX box)=0;          //Define a box
    virtual LI_response define(FORMAT format)=0;    //Define a format
    virtual LI_response modify(BOX box)=0;          //Modify a box
    virtual LI_response modify(LENGTH X_SHIFT, LENGTH Y_SHIFT, BOX
            box)=0;
    virtual LI_response modify(FORMAT format)=0;    //Modify a format
    virtual LI_response remove(FIXED_ID); //Remove image from a position
    virtual LI_response remove(BOX box,Bool def=FALSE,Bool all=FALSE);
                                                //Del box
    virtual LI_response remove(FORMAT format,Bool def=FALSE,Bool
            all=FALSE);
    virtual LI_response remove(IMAGE image,Bool def=FALSE,Bool all=FALSE);
    virtual LI_response remove_fixed_images(void);  //Remove all fixed images
    virtual LI_response remove_all(Bool def=FALSE); //Delete everything
    // Manipulation Commands
    virtual LI_response reserve(IMAGE image)=0;     //Reserve memory
    virtual LI_response store(void)=0;              //Store next image
    virtual LI_response store(FIXED_ID)=0;          //Store image for a position
    virtual LI_response store(IMAGE image)=0;       //Store an image
    virtual LI_response store(TEST_IMAGE image)=0;  //Store a test image
    virtual LI_response store(STRING string)=0;     //Store a test image
    virtual LI_response transfer(IMAGE image)=0;    //Transfer an image
    // Mailbox Commands
    virtual LI_response clear(MAILBOX mbox)=0;      //Clear a mailbox
    virtual LI_response receive(MAILBOX mbox,char *msg)=0;
                                                //Get a msg into a mbox
    virtual LI_response send(MAILBOX mbox,char *msg)=0;
                                                //Send a message to a mbox
    // Process configuration / status commands
    virtual LI_response set(PARAMETERS ptr)=0;      //set imaging parameters
    virtual LI_response show_fixed(PARAMETERS *);
    virtual LI_response show_mem(PARAMETERS *ptr);  //show image memory
    virtual LI_response show_PARAMETERS *ptr)=0;    //show imag. params.
    virtual LI_response show(IMAGE *ptr)=0;         //show info of image
    virtual LI_response show(Film_Processor *ptr)=0;    //show status of a FP
    virtual LI_response show(Image_Mgmnt_System *ptr)=0; //show IMS status
    virtual LI_response show(Printer *ptr)=0;       //show status of Printer
    virtual LI_response show(Job *ptr)=0;           //show status of a Job
    virtual LI_response show(Xfr *ptr)=0;           //show status of Xfr job
    virtual LI_response show_formats(char *ptr)=0;  //string of defined frmts
    virtual LI_response show_images(char *ptr)=0;   //string of defined images
    virtual LI_response show_con_tables(char *ptr)=0;   //string of cont tables
    virtual LI_response show_ccon_tables(char *ptr)=0;  //string of color con tbls
};
```

Output Driver Base-Class Protocol

The output driver component 24 provides five remote procedure calls for output interpreter component 22. With the five remote procedure calls, output interpreter component 22 can directly interface with an output imaging device 18, such as a laser imager. Each of the five remote procedure calls is described below:

| 1. | xmit_message | Parameters:<br>message<br>Returns:<br>Driver return code | Type:<br>char *<br>Type:<br>DRIVER_RC |
|---|---|---|---|

The above RPC passes output driver component 24 a message to transmit to input imaging device 12 via pipeline 30. The output component 26 handles all requirements for communication with output imaging device 18.

| 2. | receive_message | Parameters:<br>message<br>Returns:<br>Driver return code | Type:<br>char *<br>Type:<br>DRIVER_RC |
|---|---|---|---|

The above RPC retrieves a message from output driver component 26 that has been sent from output imaging device 18. Again, output driver component 26 handles all requirements for communication with output imaging device.

| 3. | set_xmit_timeout | Parameters:<br>timeout<br>Returns:<br>Driver return code | Type:<br>int<br>Type:<br>DRIVER_RC |
|---|---|---|---|

The above RPC sets the timeout value that output driver component 26 should use when sending to the output imaging device 18.

| 4. | set_async_func | Parameters:<br>client ptr<br>method ptr<br>Returns:<br>Driver return code | Type:<br>FE_CLIENT_PTR<br>FE_METHOD_PTR<br>Type:<br>DRIVER_PC |
|---|---|---|---|

The above RPC gives output driver component 26 a handle to the asynchronous handler of the client component, output interpreter component 24. The above RPC is used to inform the client component of asynchronous events that have occurred. The only event is MSG_PENDING which indicates a message has been fully received from output imaging device 18 and is ready for the output interpreter component 24.

| 5. | set_debug_level | Parameters:<br>debug level<br>Returns:<br>Driver return code | Type:<br>DEBUG_LEVEL<br>Type:<br>DRIVER_RC |
|---|---|---|---|

The above RPC allows the client component to set the debug level for output driver component. The debug levels are NO_DEBUG, LOW_DEBUG, MEDIUM_DEBUG, and HIGH_DEBUG. This parameter affects the information displayed during debugging.

As noted above, each RPC returns one of three driver return codes: (1) RPC_OK, (2) PORT_BUSY, and (3) NO_MESSAGE. The driver return codes can be defined in C++ code as follows:

```
//Set return types for I/O Driver interface
typedef enum {
RPC_OK,            //RPC was issued and acknowledged
PORT_BUSY,         //Transmit RPC failed, port already transmitting
NO_MESSAGE         //Receive RPC failed, no message pending
} DRIVER_RC;
```

The actual base class protocol for output driver component 26 can be defined in C++ code as follows:

```
class OUTPUT_INTERFACE
{
public:
    OUTPUT_INTERFACE(PORT_ID newport);
    ~OUTPUT_INTERFACE(void);
    virtual DRIVER_RC xmit_message(char *message) = 0;
    virtual DRIVER_RC receive_message(char *message) =0;
    virtual DRIVER_RC set_xmit_timeout(int timeout) =0;
    virtual DRIVER_RC set_async_func(CLIENT_PTR,
            CLIENT_METHOD_PTR)=0; //
    PORT_ID port;      //This port ID
```

As the embodiments of the invention have already been described, additional advantages and modifications will readily occur to those skilled in the art from consideration of the specification and practice of the invention as is disclosed herein. Therefore, the specification and examples should be considered exemplary only, with the true scope and spirit of the invention indicated by the following claims.

What is claimed is:

1. A software system for communicating medical image information between at least one of a plurality of different input imaging devices and at least one of a plurality of different laser imagers via a network interface, the software system comprising:

one or more network driver components, each of the network driver components being configured to receive medical image information from one of the input imaging devices via a network interface, the medical image information being received according to one of a plurality of different network driver protocols, wherein each of the network driver protocols is specifically associated with one of the input imaging devices;

one or more network interpreter components, each of the network interpreter components being configured to generate first imaging requests based on the medical image information received by one of the network driver components, the first imaging requests being generated according to one of a plurality of different network interpreter protocols, wherein each of the network interpreter protocols is specifically associated with one of the input imaging devices;

one or more output interpreter components, each of the output interpreter components being configured to generate second imaging requests based on the first imaging requests generated by one of the network interpreter components, the second imaging requests being generated according to one of a plurality of different output interpreter protocols, wherein each of the output interpreter protocols is specifically associated with one of the laser imagers;

one or more output driver components, each of the output driver components being configured to communicate the second imaging requests generated by one of the output interpreter components to one of the laser imagers, the second imaging requests being communicated according to one of a plurality of different output driver protocols, wherein each of the output driver protocols is specifically associated with one of the laser imagers;

one or more network executive components, each of the network executive components communicatively interconnecting one of the network driver components and one of the network interpreter components; and an interface executive component for defining one or more network communication pipelines, each of the pipelines communicatively interconnecting one of the input imaging devices, one of the network executive components, one of the output interpreter components, one of the output driver components, and one of the laser imagers.

2. The software system of claim 1, wherein:

each of said network driver components includes a first interface for communicating the image information to one of said network interpreter components according to a first base-class protocol generic to each of said network driver components and understood by each of said network interpreter components;

each of said network interpreter components includes a second interface for communicating the first imaging requests to one of said output interpreter components according to a second base-class protocol generic to each of said network interpreter components and understood by each of said output interpreter components; and each of said output interpreter components includes a third interface for communicating the second imaging requests to one of said output driver components according to a third base-class protocol generic to each of said output interpreter components and understood by each of said output driver components.

3. The software system of claim 2, wherein each of said first base-class protocol, said second base-class protocol, and said third base-class protocol is defined according to an object-oriented hierarchy.

4. The software system of claim 2, wherein:

each of said output driver components is further configured to receive first responses to the second imaging requests from one of said output imaging devices, said first responses being received according to one of said output driver protocols;

each of said output interpreter components is further configured to generate second responses based on said first responses received by one of said output driver components, said second responses being generated according to one of said output interpreter protocols;

each of said network interpreter components is further configured to generate third responses based on said second responses generated by one of said output interpreter components, said second responses being generated according to one of said network interpreter protocols; and each of said network driver components is further configured to communicate said third responses generated by one of said network interpreter components to one of said input imaging devices, said third responses being communicated according to one of said network driver protocols; and each of said pipelines defined by said interface executive component is a bi-directional pipeline communicatively interconnecting one of said input imaging devices, one of said network executive components, one of said output interpreter components, one of said output driver components, and one of said laser imagers for bi-directional communication between one of said input imaging devices and one of said output imaging devices.

5. The software system of claim 4, wherein:

each of said output driver components includes a fourth interface for communicating the first responses to one of said output interpreter components according to a fourth base-class protocol generic to each of said output driver components and understood by each of said output interpreter components;

the third interface of each of said output interpreter components is configured to communicate the second response to one of said network interpreter components according to said third base-class protocol generic to each of said output interpreter components and understood by each of said network interpreter components; and the second interface of each of said network interpreter components is configured to communicate the first response to one of said network driver components according to said second base-class protocol generic to each of said network interpreter components and understood by each of said network driver components.

6. The software system of claim 5, wherein said interface executive component defines each of said pipelines according to a client-server relationship such that each of said network interpreter components is a client of one of said network driver components, each of said network interpreter components is a client of one of said output interpreter components, each of said output interpreter components is a client of one of said output driver components, and said interface executive component is a client of each of said network executive components.

7. The software system of claim 6, wherein communication between said network interpreter components, said network driver components, and said output interpreter components is carried out by remote procedure calls generated by said network interpreter components and executed by said network driver components and said output interpreter components, wherein communication between said output interpreter components and said output driver components is carried out by remote procedure calls generated by said output interpreter components and executed by said output driver components, and wherein communication between said interface executive component and said network executive components is carried out by remote procedure calls generated by said interface executive component and executed by said network executive component.

8. The software system of claim 1, wherein at least one of the input imaging devices includes a medical imaging modality.

9. A software system for communicating medical image information between at least one of a plurality of different medical imaging modalities and at least one of a plurality of different laser imagers via a network interface, the software system comprising:

one or more network interface components, each of the network interface components being configured to receive medical image information from one of the medical imaging modalities via the network interface, the medical image information being received according to one of a plurality of different network interface protocols, wherein each of the network interface protocols is specifically associated with one of the medical imaging modalities, and to generate first imaging requests based on the received medical image information, the first imaging requests being generated according to the one of the network interface protocols;

one or more output interface components, each of the output interface components being configured to generate second imaging requests based on the first imaging requests generated by one of the network interface components, the second imaging requests being generated according to one of a plurality of different output interface protocols, wherein each of the output interface protocols is specifically associated with one of the laser imagers, and to communicate the second imaging requests generated by one of the output interface components to one of the laser imagers, the second imaging requests being communicated according to the one of the output interface protocols; and an interface executive component for defining one or more communication pipelines, each of the pipelines communicatively interconnecting one of the medical imaging modalities, one of the network interface components, one of the output interface components, and one of the laser imagers.

10. The software system of claim 9, wherein each of said network interface components includes a first interface for communicating the first imaging requests to one of said output interface components according to a base-class protocol generic to each of said network interface components and understood by each of said output interface components.

11. The software system of claim 10, wherein the base-class protocol is defined according to an object-oriented hierarchy.

12. The software system of claim 10, wherein:

each of said output interface components is further configured to receive first responses to the second imaging requests from one of said laser imagers, said first responses being received according to one of said output interface protocols, and to generate second responses based on said first responses, said second responses being generated according to one of said output interface protocols; and each of said network interface components is further configured to generate third responses based on said second responses generated by one of said output interface components, said third responses being generated according to one of said network interface protocols, and to communicate said third responses to one of said input imaging devices, said third responses being communicated according to one of said network interface protocols; and each of said pipelines defined by said interface executive component is a bi-directional pipeline communicatively interconnecting one of said input imaging devices, one of said network interface components, one of said output interface components, and one of said laser imagersfor bi-directional communication between one of said medical imaging modalities and one of said laser imagers.

13. The software system of claim 12, wherein each of said output interface components includes a second interface for communicating the second responses to one of said network interface components according to a second base-class protocol generic to each of said output interface components and understood by each of said network interface components.

14. The software system of claim 12, wherein said interface executive component defines each of said pipelines according to a client-server relationship such that each of said network interface components is a client of one of said output interface components, and said interface executive component is a client of each of said network interface components.

15. The software system of claim 14, wherein communication between said network interface components and said output interface components is carried out by remote procedure calls generated by said network interface components and executed by said output interface components, and wherein communication between said interface executive component, said network interface components, and said output interface components is carried out by remote procedure calls generated by said interface executive component and executed by said network interface components.

* * * * *